(12) United States Patent
Sakano

(10) Patent No.: US 7,022,499 B2
(45) Date of Patent: *Apr. 4, 2006

(54) NUCLEIC ACIDS ENCODING DIFFERENTIATION INHIBITOR DELTA 2

(75) Inventor: Seiji Sakano, Shizuoka (JP)

(73) Assignee: Asahi Kasei Kabushiki Kaisha, Osaka (JP)

( * ) Notice: Subject to any disclaimer, the term of this patent is extended or adjusted under 35 U.S.C. 154(b) by 281 days.

This patent is subject to a terminal disclaimer.

(21) Appl. No.: 10/241,476

(22) Filed: Sep. 12, 2002

(65) Prior Publication Data

US 2003/0049788 A1 Mar. 13, 2003

Related U.S. Application Data

(62) Division of application No. 09/423,753, filed as application No. PCT/JP98/02104 on May 13, 1998, now Pat. No. 6,664,098.

(30) Foreign Application Priority Data

May 14, 1997 (JP) ............................................. 9-124064

(51) Int. Cl.
*C12N 15/09* (2006.01)

(52) U.S. Cl. ................... 435/69.1; 435/320.1; 435/366; 536/23.5; 530/350

(58) Field of Classification Search ................. 536/23.5; 530/350; 435/320.1, 69.1, 325
See application file for complete search history.

(56) References Cited

U.S. PATENT DOCUMENTS 6,121,045 A * 9/2000 McCarthy et al. .......... 435/325
6,291,210 B1    9/2001 Sakano et al.

FOREIGN PATENT DOCUMENTS

| EP | 0 861 894 | 9/1998 |
|---|---|---|
| WO | 92/19734 | 11/1992 |
| WO | 93/12141 | 6/1993 |
| WO | 96/27610 | 9/1996 |
| WO | 97/01571 | 1/1997 |
| WO | 97/19172 | 5/1997 |

OTHER PUBLICATIONS

See Boggs et al., Experimental Hematology, vol., 14, No. 10, pp. 988–994, 1986.*
Shutter et al., "D114, a novel Notch ligand expressed in arterial Endothelium", Genes and Development, vol. 14, No. 11, Jun. 1, 2000, XP–002237111, pp. 1313–1318.
"Delta–like protein 4 precursor (Drosohpila Delta homolog 4)" retrieved from SWISSPROT, Database Accession No. Q9NR61; Q9NQT9, XP–002268417, Mar. 15, 2004.
Sally L. Dunwoodie et al., "Mouse DII3: a novel divergent *Delta* gene which may complement the function of other *Delta* homologues during early pattern formation in the mouse embryo", Development, Company of Biologists, vol. 124, No. 16, Aug. 1997, XP–002126914, pp. 3065–3076.
Berthold Bettenhausen et al., "Transient and restricted expression during mouse embryogenesis of *DIII*, a murine gene closely related to *Drosophila Delta*", Development, Company of Biologists, vol. 121, No. 8, Aug. 1995, XP–002168988, pp. 2407–2418.
"Delta–like protein 1 precursor (Drosophila Delta homolog 1) (Delta 1)" retrieved from SWISSPROT, Database Accession No. Q61483, XP–002268418, Nov. 1, 1997.
"Delta–like protein 1 precursor (Drosophila Delta homolog 1) (Delta1)" retrieved from SWISSPROT, Database Accession No. P97677, XP–002268419, Nov. 1, 1997.
Henrique D. et al., "Expression of a *Delta* homologue in prospective neurons in the chick", Nature, MacMillan Journals Ltd., vol. 375, Jun. 29, 1995, XP–002924718, pp. 787–790.
"C–delta–1" retrieved from SWISSPROT, Database Accession No. Q90656, XP–002268420, Nov. 1, 1996.
Chitnis A. et al., "Primary neurogenesis in *Xenopus* embryos regulated by a homologue of the *Drosophila* neurogenic gene *Delta*", Nature, MacMillan Journals Ltd., vol. 375, Jun. 29, 1995, XP–000999218, pp. 761–766.

* cited by examiner

*Primary Examiner*—Elizabeth Kemmerer
*Assistant Examiner*—Eileen B. O'Hara
(74) *Attorney, Agent, or Firm*—Young & Thompson

(57) ABSTRACT

Amino acids constituting a physiologically active molecule human delta 2; a gene arrangement thereof; and an antibody thereto. The human delta 2 molecule, at least the amino acid sequence described in SEQ ID NO: 1 of the sequence listing, functions as a chemical useful for proliferation of undifferentiated blood cells and inhibition of differentiation, and hence can be utilized as pharmaceuticals and medical supplies.

10 Claims, 3 Drawing Sheets

SEQUENCE LISTING

<160> NUMBER OF SEQ ID NOS: 27

<210> SEQ ID NO 1
<211> LENGTH: 191
<212> TYPE: PRT
<213> ORGANISM: Homo sapiens

<400> SEQUENCE: 1

Ser Gly Val Phe Gln Leu Gln Leu Gln Glu Phe Ile Asn Glu Arg Gly
 1               5                  10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys
        35                  40                  45

Thr Phe Gly Thr Val Ser Thr Pro Val Leu Gly Thr Asn Ser Phe Ala
    50                  55                  60

Val Arg Asp Asp Ser Ser Gly Gly Gly Arg Asn Pro Leu Gln Leu Pro
65                  70                  75                  80

Phe Asn Phe Thr Trp Pro Gly Thr Phe Ser Leu Ile Ile Glu Ala Trp
                85                  90                  95

His Ala Pro Gly Asp Asp Leu Arg Pro Glu Ala Leu Pro Pro Asp Ala
            100                 105                 110

Leu Ile Ser Lys Ile Ala Ile Gln Gly Ser Leu Ala Val Gly Gln Asn
        115                 120                 125

Trp Leu Leu Asp Glu Gln Thr Ser Thr Leu Thr Arg Leu Arg Tyr Ser
    130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys
            180                 185                 190

<210> SEQ ID NO 2
<211> LENGTH: 500
<212> TYPE: PRT
<213> ORGANISM: Homo sapiens

<400> SEQUENCE: 2

Ser Gly Val Phe Gln Leu Gln Leu Gln Glu Phe Ile Asn Glu Arg Gly
 1               5                  10                  15

Val Leu Ala Ser Gly Arg Pro Cys Glu Pro Gly Cys Arg Thr Phe Phe
            20                  25                  30

Arg Val Cys Leu Lys His Phe Gln Ala Val Val Ser Pro Gly Pro Cys

```
                   35                  40                  45
Thr Phe Gly Thr Val Ser Thr Pro Val Leu Gly Thr Asn Ser Phe Ala
 50                  55                  60

Val Arg Asp Asp Ser Ser Gly Gly Arg Asn Pro Leu Gln Leu Pro
 65                  70                  75                  80

Phe Asn Phe Thr Trp Pro Gly Thr Phe Ser Leu Ile Ile Glu Ala Trp
                     85                  90                  95

His Ala Pro Gly Asp Asp Leu Arg Pro Glu Ala Leu Pro Pro Asp Ala
                100                 105                 110

Leu Ile Ser Lys Ile Ala Ile Gln Gly Ser Leu Ala Val Gly Gln Asn
                115                 120                 125

Trp Leu Leu Asp Glu Gln Thr Ser Thr Leu Thr Arg Leu Arg Tyr Ser
            130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys Gln
                180                 185                 190

Gln Pro Ile Cys Leu Ser Gly Cys His Glu Gln Asn Gly Tyr Cys Ser
                195                 200                 205

Lys Pro Ala Glu Cys Leu Cys Arg Pro Gly Trp Gln Gly Arg Leu Cys
210                 215                 220

Asn Glu Cys Ile Pro His Asn Gly Cys Arg His Gly Thr Cys Ser Thr
225                 230                 235                 240

Pro Trp Gln Cys Thr Cys Asp Glu Gly Trp Gly Gly Leu Phe Cys Asp
                245                 250                 255

Gln Asp Leu Asn Tyr Cys Thr His His Ser Pro Cys Lys Asn Gly Ala
                260                 265                 270

Thr Cys Ser Asn Ser Gly Gln Arg Ser Tyr Thr Cys Thr Cys Arg Pro
                275                 280                 285

Gly Tyr Thr Gly Val Asp Cys Glu Leu Glu Leu Ser Glu Cys Asp Ser
290                 295                 300

Asn Pro Cys Arg Asn Gly Gly Ser Cys Lys Asp Gln Glu Asp Gly Tyr
305                 310                 315                 320

His Cys Leu Cys Pro Pro Gly Tyr Tyr Gly Leu His Cys Glu His Ser
                325                 330                 335

Thr Leu Ser Cys Ala Asp Ser Pro Cys Phe Asn Gly Gly Ser Cys Arg
                340                 345                 350

Glu Arg Asn Gln Gly Ala Asn Tyr Ala Cys Glu Cys Pro Pro Asn Phe
                355                 360                 365

Thr Gly Ser Asn Cys Glu Lys Lys Val Asp Arg Cys Thr Ser Asn Pro
            370                 375                 380

Cys Ala Asn Gly Gly Gln Cys Leu Asn Arg Gly Pro Ser Arg Met Cys
385                 390                 395                 400

Arg Cys Arg Pro Gly Phe Thr Gly Thr Tyr Cys Glu Leu His Val Ser
                405                 410                 415

Asp Cys Ala Arg Asn Pro Cys Ala His Gly Gly Thr Cys His Asp Leu
                420                 425                 430

Glu Asn Gly Leu Met Cys Thr Cys Pro Ala Gly Phe Ser Gly Arg Arg
            435                 440                 445

Cys Glu Val Arg Thr Ser Ile Asp Ala Cys Ala Ser Ser Pro Cys Phe
450                 455                 460
```

```
Asn Arg Ala Thr Cys Tyr Thr Asp Leu Ser Thr Asp Thr Phe Val Cys
465                 470                 475                 480

Asn Cys Pro Tyr Gly Phe Val Gly Ser Arg Cys Glu Phe Pro Val Gly
                485                 490                 495

Leu Pro Pro Ser
            500

<210> SEQ ID NO 3
<211> LENGTH: 659
<212> TYPE: PRT
<213> ORGANISM: Homo sapiens

<400> SEQUENCE: 3

Ser Gly Val Phe Gln Leu Gln Leu Gln Glu Phe Ile Asn Glu Arg Gly
 1               5                  10                  15

Val Leu Ala Ser Gly Arg Pro Cys Glu Pro Gly Cys Arg Thr Phe Phe
                20                  25                  30

Arg Val Cys Leu Lys His Phe Gln Ala Val Val Ser Pro Gly Pro Cys
                35                  40                  45

Thr Phe Gly Thr Val Ser Thr Pro Val Leu Gly Thr Asn Ser Phe Ala
    50                  55                  60

Val Arg Asp Asp Ser Ser Gly Gly Arg Asn Pro Leu Gln Leu Pro
 65                 70                  75                  80

Phe Asn Phe Thr Trp Pro Gly Thr Phe Ser Leu Ile Ile Glu Ala Trp
                85                  90                  95

His Ala Pro Gly Asp Asp Leu Arg Pro Glu Ala Leu Pro Pro Asp Ala
                100                 105                 110

Leu Ile Ser Lys Ile Ala Ile Gln Gly Ser Leu Ala Val Gly Gln Asn
                115                 120                 125

Trp Leu Leu Asp Glu Gln Thr Ser Thr Leu Thr Arg Leu Arg Tyr Ser
    130                 135                 140

Tyr Arg Val Ile Cys Ser Asp Asn Tyr Tyr Gly Asp Asn Cys Ser Arg
145                 150                 155                 160

Leu Cys Lys Lys Arg Asn Asp His Phe Gly His Tyr Val Cys Gln Pro
                165                 170                 175

Asp Gly Asn Leu Ser Cys Leu Pro Gly Trp Thr Gly Glu Tyr Cys Gln
                180                 185                 190

Gln Pro Ile Cys Leu Ser Gly Cys His Glu Gln Asn Gly Tyr Cys Ser
                195                 200                 205

Lys Pro Ala Glu Cys Leu Cys Arg Pro Gly Trp Gln Gly Arg Leu Cys
    210                 215                 220

Asn Glu Cys Ile Pro His Asn Gly Cys Arg His Gly Thr Cys Ser Thr
225                 230                 235                 240

Pro Trp Gln Cys Thr Cys Asp Glu Gly Trp Gly Gly Leu Phe Cys Asp
                245                 250                 255

Gln Asp Leu Asn Tyr Cys Thr His His Ser Pro Cys Lys Asn Gly Ala
                260                 265                 270

Thr Cys Ser Asn Ser Gly Gln Arg Ser Tyr Thr Cys Thr Cys Arg Pro
    275                 280                 285

Gly Tyr Thr Gly Val Asp Cys Glu Leu Glu Leu Ser Glu Cys Asp Ser
    290                 295                 300

Asn Pro Cys Arg Asn Gly Gly Ser Cys Lys Asp Gln Glu Asp Gly Tyr
305                 310                 315                 320

His Cys Leu Cys Pro Pro Gly Tyr Tyr Gly Leu His Cys Glu His Ser
```

```
              325                 330                 335
Thr Leu Ser Cys Ala Asp Ser Pro Cys Phe Asn Gly Gly Ser Cys Arg
            340                 345                 350
Glu Arg Asn Gln Gly Ala Asn Tyr Ala Cys Glu Cys Pro Pro Asn Phe
        355                 360                 365
Thr Gly Ser Asn Cys Glu Lys Lys Val Asp Arg Cys Thr Ser Asn Pro
    370                 375                 380
Cys Ala Asn Gly Gly Gln Cys Leu Asn Arg Gly Pro Ser Arg Met Cys
385                 390                 395                 400
Arg Cys Arg Pro Gly Phe Thr Gly Thr Tyr Cys Glu Leu His Val Ser
                405                 410                 415
Asp Cys Ala Arg Asn Pro Cys Ala His Gly Gly Thr Cys His Asp Leu
            420                 425                 430
Glu Asn Gly Leu Met Cys Thr Cys Pro Ala Gly Phe Ser Gly Arg Arg
        435                 440                 445
Cys Glu Val Arg Thr Ser Ile Asp Ala Cys Ala Ser Ser Pro Cys Phe
    450                 455                 460
Asn Arg Ala Thr Cys Tyr Thr Asp Leu Ser Thr Asp Thr Phe Val Cys
465                 470                 475                 480
Asn Cys Pro Tyr Gly Phe Val Gly Ser Arg Cys Glu Phe Pro Val Gly
                485                 490                 495
Leu Pro Pro Ser Phe Pro Trp Val Ala Val Ser Leu Gly Val Gly Leu
            500                 505                 510
Ala Val Leu Leu Val Leu Leu Gly Met Val Ala Val Ala Val Arg Gln
        515                 520                 525
Leu Arg Leu Arg Arg Pro Asp Asp Gly Ser Arg Glu Ala Met Asn Asn
    530                 535                 540
Leu Ser Asp Phe Gln Lys Asp Asn Leu Ile Pro Ala Ala Gln Leu Lys
545                 550                 555                 560
Asn Thr Asn Gln Lys Lys Glu Leu Glu Val Asp Cys Gly Leu Asp Lys
                565                 570                 575
Ser Asn Cys Gly Lys Gln Gln Asn His Thr Leu Asp Tyr Asn Leu Ala
            580                 585                 590
Pro Gly Pro Leu Gly Arg Gly Thr Met Pro Gly Lys Phe Pro His Ser
        595                 600                 605
Asp Lys Ser Leu Gly Glu Lys Ala Pro Leu Arg Leu His Ser Glu Lys
    610                 615                 620
Pro Glu Cys Arg Ile Ser Ala Ile Cys Ser Pro Arg Asp Ser Met Tyr
625                 630                 635                 640
Gln Ser Val Cys Leu Ile Ser Glu Glu Arg Asn Glu Cys Val Ile Ala
                645                 650                 655
Thr Glu Val

<210> SEQ ID NO 4
<211> LENGTH: 3339
<212> TYPE: DNA
<213> ORGANISM: Homo sapiens
<220> FEATURE:
<221> NAME/KEY: CDS
<222> LOCATION: (277)..(2331)
<220> FEATURE:
<221> NAME/KEY: sig_peptide
<222> LOCATION: (277)..(354)
<220> FEATURE:
<221> NAME/KEY: mat_peptide
<222> LOCATION: (355)..(2331)
```

<400> SEQUENCE: 4

```
gccgccttgg tgcagcgtac accggcacta gcccgcttgc agccccagga ttagacagaa      60
gacgcgtcct cggcgcggtc gccgcccagc cgtagtcacc tggattacct acagcggcag     120
ctgcagcgga gccagcgaga aggccaaagg ggagcagcgt cccgagagga gcgcctcttt     180
tcagggaccc cgccggctgg cggacgcgcg ggaaagcggc gtcgcgaaca gagccagatt     240
gagggcccgc gggtggagag agcgacgccc gagggg atg gcg gca gcg tcc cgg      294
                                        Met Ala Ala Ala Ser Arg
                                            -25 agc gcc tct ggc tgg gcg cta ctg ctg ctg gtg gca ctt tgg cag cag       342
Ser Ala Ser Gly Trp Ala Leu Leu Leu Leu Val Ala Leu Trp Gln Gln
-20              -15                 -10                 -5 cgc gcg gcc ggc tcc ggc gtc ttc cag ctg cag ctg cag gag ttc atc       390
Arg Ala Ala Gly Ser Gly Val Phe Gln Leu Gln Leu Gln Glu Phe Ile
         -1   1              5                  10 aac gag cgc ggc gta ctg gcc agt ggg cgg cct tgc gag ccc ggc tgc       438
Asn Glu Arg Gly Val Leu Ala Ser Gly Arg Pro Cys Glu Pro Gly Cys
         15                  20                  25 cgg act ttc ttc cgc gtc tgc ctt aag cac ttc cag gcg gtc gtc tcg       486
Arg Thr Phe Phe Arg Val Cys Leu Lys His Phe Gln Ala Val Val Ser
     30                  35                  40 ccc gga ccc tgc acc ttc ggg acc gtc tcc acg ccg gta ttg ggc acc       534
Pro Gly Pro Cys Thr Phe Gly Thr Val Ser Thr Pro Val Leu Gly Thr
 45                  50                  55                  60 aac tcc ttc gct gtc cgg gac gac agt agc ggc ggg ggg cgc aac cct       582
Asn Ser Phe Ala Val Arg Asp Asp Ser Ser Gly Gly Gly Arg Asn Pro
                 65                  70                  75 ctc caa ctg ccc ttc aat ttc acc tgg ccg ggt acc ttc tcg ctc atc       630
Leu Gln Leu Pro Phe Asn Phe Thr Trp Pro Gly Thr Phe Ser Leu Ile
             80                  85                  90 atc gaa gct tgg cac gcg cca gga gac gac ctg cgg cca gag gcc ttg       678
Ile Glu Ala Trp His Ala Pro Gly Asp Asp Leu Arg Pro Glu Ala Leu
         95                 100                 105 cca cca gat gca ctc atc agc aag atc gcc atc cag ggc tcc cta gct       726
Pro Pro Asp Ala Leu Ile Ser Lys Ile Ala Ile Gln Gly Ser Leu Ala
    110                 115                 120 gtg ggt cag aac tgg tta ttg gat gag caa acc agc acc ctc aca agg       774
Val Gly Gln Asn Trp Leu Leu Asp Glu Gln Thr Ser Thr Leu Thr Arg
125                 130                 135                 140 ctg cgc tac tct tac cgg gtc atc tgc agt gac aac tac tat gga gac       822
Leu Arg Tyr Ser Tyr Arg Val Ile Cys Ser Asp Asn Tyr Tyr Gly Asp
                145                 150                 155 aac tgc tcc cgc ctg tgc aag aag cgc aat gac cac ttc ggc cac tat       870
Asn Cys Ser Arg Leu Cys Lys Lys Arg Asn Asp His Phe Gly His Tyr
            160                 165                 170 gtg tgc cag cca gat ggc aac ttg tcc tgc ctg ccc ggt tgg act ggg       918
Val Cys Gln Pro Asp Gly Asn Leu Ser Cys Leu Pro Gly Trp Thr Gly
        175                 180                 185 gaa tat tgc caa cag cct atc tgt ctt tcg ggc tgt cat gaa cag aat       966
Glu Tyr Cys Gln Gln Pro Ile Cys Leu Ser Gly Cys His Glu Gln Asn
    190                 195                 200 ggc tac tgc agc aag cca gca gag tgc ctc tgc cgc cca ggc tgg cag      1014
Gly Tyr Cys Ser Lys Pro Ala Glu Cys Leu Cys Arg Pro Gly Trp Gln
205                 210                 215                 220 ggc cgg ctg tgt aac gaa tgc atc ccc cac aat ggc tgt cgc cac ggc      1062
Gly Arg Leu Cys Asn Glu Cys Ile Pro His Asn Gly Cys Arg His Gly
                225                 230                 235 acc tgc agc act ccc tgg caa tgt act tgt gat gag ggc tgg gga ggc      1110
Thr Cys Ser Thr Pro Trp Gln Cys Thr Cys Asp Glu Gly Trp Gly Gly
```

-continued

| | | | | | | | | | | | | | | | |
|---|---|---|---|---|---|---|---|---|---|---|---|---|---|---|---|
| Thr | Cys | Ser | Thr | Pro | Trp | Gln | Cys | Thr | Cys | Asp | Glu | Gly | Trp | Gly | Gly |
| | | | 240 | | | | 245 | | | | 250 | | | | |

```
ctg ttt tgt gac caa gat ctc aac tac tgc acc cac cac tcc cca tgc      1158
Leu Phe Cys Asp Gln Asp Leu Asn Tyr Cys Thr His His Ser Pro Cys
        255                 260                 265 aag aat ggg gca acg tgc tcc aac agt ggg cag cga agc tac acc tgc      1206
Lys Asn Gly Ala Thr Cys Ser Asn Ser Gly Gln Arg Ser Tyr Thr Cys
    270                 275                 280 acc tgt cgc cca ggc tac act ggt gtg gac tgt gag ctg gag ctc agc      1254
Thr Cys Arg Pro Gly Tyr Thr Gly Val Asp Cys Glu Leu Glu Leu Ser
285                 290                 295                 300 gag tgt gac agc aac ccc tgt cgc aat gga ggc agc tgt aag gac cag      1302
Glu Cys Asp Ser Asn Pro Cys Arg Asn Gly Gly Ser Cys Lys Asp Gln
                305                 310                 315 gag gat ggc tac cac tgc ctg tgt cct ccg ggc tac tat ggc ctg cat      1350
Glu Asp Gly Tyr His Cys Leu Cys Pro Pro Gly Tyr Tyr Gly Leu His
            320                 325                 330 tgt gaa cac agc acc ttg agc tgc gcc gac tcc ccc tgc ttc aat ggg      1398
Cys Glu His Ser Thr Leu Ser Cys Ala Asp Ser Pro Cys Phe Asn Gly
        335                 340                 345 ggc tcc tgc cgg gag cgc aac cag ggg gcc aac tat gct tgt gaa tgt      1446
Gly Ser Cys Arg Glu Arg Asn Gln Gly Ala Asn Tyr Ala Cys Glu Cys
350                 355                 360 ccc ccc aac ttc acc ggc tcc aac tgc gag aag aaa gtg gac agg tgc      1494
Pro Pro Asn Phe Thr Gly Ser Asn Cys Glu Lys Lys Val Asp Arg Cys
365                 370                 375                 380 acc agc aac ccc tgt gcc aac ggg gga cag tgc ctg aac cga ggt cca      1542
Thr Ser Asn Pro Cys Ala Asn Gly Gly Gln Cys Leu Asn Arg Gly Pro
                385                 390                 395 agc cgc atg tgc cgc tgc cgt cct gga ttc acg ggc acc tac tgt gaa      1590
Ser Arg Met Cys Arg Cys Arg Pro Gly Phe Thr Gly Thr Tyr Cys Glu
            400                 405                 410 ctc cac gtc agc gac tgt gcc cgt aac cct tgc gcc cac ggt ggc act      1638
Leu His Val Ser Asp Cys Ala Arg Asn Pro Cys Ala His Gly Gly Thr
        415                 420                 425 tgc cat gac ctg gag aat ggg ctc atg tgc acc tgc cct gcc ggc ttc      1686
Cys His Asp Leu Glu Asn Gly Leu Met Cys Thr Cys Pro Ala Gly Phe
430                 435                 440 tct ggc cga cgc tgt gag gtg cgg aca tcc atc gat gcc tgt gcc tcg      1734
Ser Gly Arg Arg Cys Glu Val Arg Thr Ser Ile Asp Ala Cys Ala Ser
445                 450                 455                 460 agt ccc tgc ttc aac agg gcc acc tgc tac acc gac ctc tcc aca gac      1782
Ser Pro Cys Phe Asn Arg Ala Thr Cys Tyr Thr Asp Leu Ser Thr Asp
                465                 470                 475 acc ttt gtg tgc aac tgc cct tat ggc ttt gtg ggc agc cgc tgc gag      1830
Thr Phe Val Cys Asn Cys Pro Tyr Gly Phe Val Gly Ser Arg Cys Glu
            480                 485                 490 ttc ccc gtg ggc ttg ccg ccc agc ttc ccc tgg gtg gcc gtc tcg ctg      1878
Phe Pro Val Gly Leu Pro Pro Ser Phe Pro Trp Val Ala Val Ser Leu
        495                 500                 505 ggt gtg ggg ctg gca gtg ctg ctg gta ctg ctg ggc atg gtg gca gtg      1926
Gly Val Gly Leu Ala Val Leu Leu Val Leu Leu Gly Met Val Ala Val
510                 515                 520 gct gtg cgg cag ctg cgg ctt cga cgg ccg gac gac ggc agc agg gaa      1974
Ala Val Arg Gln Leu Arg Leu Arg Arg Pro Asp Asp Gly Ser Arg Glu
525                 530                 535                 540 gcc atg aac aac ttg tcg gac ttc cag aag gac aac ctg att cct gcc      2022
Ala Met Asn Asn Leu Ser Asp Phe Gln Lys Asp Asn Leu Ile Pro Ala
                545                 550                 555
```

```
gcc cag ctt aaa aac aca aac cag aag aag gag ctg gaa gtg gac tgt    2070
Ala Gln Leu Lys Asn Thr Asn Gln Lys Lys Glu Leu Glu Val Asp Cys
            560                 565                 570 ggc ctg gac aag tcc aac tgt ggc aaa cag caa aac cac aca ttg gac    2118
Gly Leu Asp Lys Ser Asn Cys Gly Lys Gln Gln Asn His Thr Leu Asp
        575                 580                 585 tat aat ctg gcc cca ggg ccc ctg ggg cgg ggg acc atg cca gga aag    2166
Tyr Asn Leu Ala Pro Gly Pro Leu Gly Arg Gly Thr Met Pro Gly Lys
    590                 595                 600 ttt ccc cac agt gac aag agc tta gga gag aag gcg cca ctg cgg tta    2214
Phe Pro His Ser Asp Lys Ser Leu Gly Glu Lys Ala Pro Leu Arg Leu
605                 610                 615                 620 cac agt gaa aag cca gag tgt cgg ata tca gcg ata tgc tcc ccc agg    2262
His Ser Glu Lys Pro Glu Cys Arg Ile Ser Ala Ile Cys Ser Pro Arg
                625                 630                 635 gac tcc atg tac cag tct gtg tgt ttg ata tca gag gag agg aat gaa    2310
Asp Ser Met Tyr Gln Ser Val Cys Leu Ile Ser Glu Glu Arg Asn Glu
            640                 645                 650 tgt gtc att gcc acg gag gta taaggcagga gcctacctgg acatccctgc       2361
Cys Val Ile Ala Thr Glu Val
            655 tcagccccgc ggctggacct tccttctgca ttgtttacat tgcatcctgg atgggacgtt  2421 tttcatatgc aacgtgctgc tctcaggagg aggagggaat ggcaggaacc ggacagactg  2481 tgaacttgcc aagagatgca ataccctttcc acacctttgg gtgtctgtct ggcatcagat 2541 tggcagctgc accaaccaga ggaacagaag agaagagaga tgccactggg cactgccctg  2601 ccagtagtgg ccttcagggg gctccttccg gggctccggc ctgttttcca gagagagtgg  2661 cagtagcccc atggggcccg gagctgctgt ggcctccact ggcatccgtg tttccaaaag  2721 tgcctttggc ccaggctcca cggcgacagt tgggcccaaa tcagaaagga gagaggggc   2781 caatgagggc agggcctcct gtgggctgga aaaccactgg gtgcgtctct tgctggggtt  2841 tgccctggag gtgaggtgag tgctcgaggg aggggagtgc tttctgcccc atgcctccaa  2901 ctactgtatg caggcctggc tctctggtct aggccctttg gcaagaatg tccgtctacc   2961 cggcttccac caccctctgg ccctgggctt ctgtaagcag acaggcagag ggcctgcccc  3021 tcccaccagc caagggtgcc aggcctaact ggggcactca gggcagtgtg ttggaaattc  3081 cactgagggg gaaatcaggt gctgcggccg cctgggccct ttcctccctc aagcccatct  3141 ccacaacctc gagcctgggc tctggtccac tactgcccca gaccaccctc aaagctggtc  3201 ttcagaaatc aataatatga gttttttattt tgttttttttt tttttttttg tagtttattt 3261 tggagtctag tatttcaata atttaagaat cagaagcact gacctttcta cattttataa  3321 cattattttg tatataat                                                 3339
```

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: CDS
<222> LOCATION: (1)..(24)

<400> SEQUENCE: 5

```
gat tat aaa gat gat gat gat aaa tga                                27
Asp Tyr Lys Asp Asp Asp Asp Lys
 1               5
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 6
tggcartgya aytgycarga                                           20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 7
atyttyttyt crcarttraa                                           20

<210> SEQ ID NO 8
<211> LENGTH: 2663
<212> TYPE: DNA
<213> ORGANISM: Homo sapiens
<220> FEATURE:
<221> NAME/KEY: CDS
<222> LOCATION: (179)..(2347)
<220> FEATURE:
<221> NAME/KEY: sig_peptide
<222> LOCATION: (179)..(241)
<220> FEATURE:
<221> NAME/KEY: mat_peptide
<222> LOCATION: (242)..(2347)

<400> SEQUENCE: 8
cttgggaaga ggcggagacc ggcttttaaa gaaagaagtc ctgggtcctg cggtctgggg    60
cgaggcaagg gcgcttttct gcccacgctc cccgtggccc atcgatcccc cgcgcgtccg   120
ccgctgttct aaggagagaa gtgggggccc ccaggctcg cgcgtggagc gaagcagc     178 atg ggc agt cgg tgc gcg ctg gcc ctg gcg gtg ctc tcg gcc ttg ctg   226
Met Gly Ser Arg Cys Ala Leu Ala Leu Ala Val Leu Ser Ala Leu Leu
    -20                 -15                 -10 tgt cag gtc tgg agc tct ggg gtg ttc gaa ctg aag ctg cag gag ttc   274
Cys Gln Val Trp Ser Ser Gly Val Phe Glu Leu Lys Leu Gln Glu Phe
-5              -1   1               5                   10 gtc aac aag aag ggg ctg ctg ggg aac cgc aac tgc tgc cgc ggg ggc   322
Val Asn Lys Lys Gly Leu Leu Gly Asn Arg Asn Cys Cys Arg Gly Gly
                15                  20                  25 gcg ggg cca ccg ccg tgc gcc tgc cgg acc ttc ttc cgc gtg tgc ctc   370
Ala Gly Pro Pro Pro Cys Ala Cys Arg Thr Phe Phe Arg Val Cys Leu
            30                  35                  40 aag cac tac cag gcc agc gtg tcc ccc gag ccg ccc tgc acc tac ggc   418
Lys His Tyr Gln Ala Ser Val Ser Pro Glu Pro Pro Cys Thr Tyr Gly
        45                  50                  55 agc gcc gtc acc ccc gtg ctg ggc gtc gac tcc ttc agt ctg ccc gac   466
Ser Ala Val Thr Pro Val Leu Gly Val Asp Ser Phe Ser Leu Pro Asp
60                  65                  70                  75 ggc ggg ggc gcc gac tcc gcg ttc agc aac ccc atc cgc ttc ccc ttc   514
Gly Gly Gly Ala Asp Ser Ala Phe Ser Asn Pro Ile Arg Phe Pro Phe
                80                  85                  90 ggc ttc acc tgg ccg ggc acc ttc tct ctg att att gaa gct ctc cac   562

```
                Gly Phe Thr Trp Pro Gly Thr Phe Ser Leu Ile Ile Glu Ala Leu His
                             95                  100                 105 aca gat tct cct gat gac ctc gca aca gaa aac cca gaa aga ctc atc          610
Thr Asp Ser Pro Asp Asp Leu Ala Thr Glu Asn Pro Glu Arg Leu Ile
        110                 115                 120 agc cgc ctg gcc acc cag agg cac ctg acg gtg ggc gag gag tgg tcc          658
Ser Arg Leu Ala Thr Gln Arg His Leu Thr Val Gly Glu Glu Trp Ser
125                 130                 135 cag gac ctg cac agc agc ggc cgc acg gac ctc aag tac tcc tac cgc          706
Gln Asp Leu His Ser Ser Gly Arg Thr Asp Leu Lys Tyr Ser Tyr Arg
140                 145                 150                 155 ttc gtg tgt gac gaa cac tac tac gga gag ggc tgc tcc gtt ttc tgc          754
Phe Val Cys Asp Glu His Tyr Tyr Gly Glu Gly Cys Ser Val Phe Cys
                160                 165                 170 cgt ccc cgg gac gat gcc ttc ggc cac ttc acc tgt ggg gag cgt ggg          802
Arg Pro Arg Asp Asp Ala Phe Gly His Phe Thr Cys Gly Glu Arg Gly
            175                 180                 185 gag aaa gtg tgc aac cct ggc tgg aaa ggg ccc tac tgc aca gag ccg          850
Glu Lys Val Cys Asn Pro Gly Trp Lys Gly Pro Tyr Cys Thr Glu Pro
        190                 195                 200 atc tgc ctg cct gga tgt gat gag cag cat gga ttt tgt gac aaa cca          898
Ile Cys Leu Pro Gly Cys Asp Glu Gln His Gly Phe Cys Asp Lys Pro
205                 210                 215 ggg gaa tgc aag tgc aga gtg ggc tgg cag ggc cgg tac tgt gac gag          946
Gly Glu Cys Lys Cys Arg Val Gly Trp Gln Gly Arg Tyr Cys Asp Glu
220                 225                 230                 235 tgt atc cgc tat cca ggc tgt ctc cat ggc acc tgc cag cag ccc tgg          994
Cys Ile Arg Tyr Pro Gly Cys Leu His Gly Thr Cys Gln Gln Pro Trp
                240                 245                 250 cag tgc aac tgc cag gaa ggc tgg ggg ggc ctt ttc tgc aac cag gac         1042
Gln Cys Asn Cys Gln Glu Gly Trp Gly Gly Leu Phe Cys Asn Gln Asp
            255                 260                 265 ctg aac tac tgc aca cac cat aag ccc tgc aag aat gga gcc acc tgc         1090
Leu Asn Tyr Cys Thr His His Lys Pro Cys Lys Asn Gly Ala Thr Cys
        270                 275                 280 acc aac acg ggc cag ggg agc tac act tgc tct tgc cgg cct ggg tac         1138
Thr Asn Thr Gly Gln Gly Ser Tyr Thr Cys Ser Cys Arg Pro Gly Tyr
285                 290                 295 aca ggt gcc acc tgc gag ctg ggg att gac gag tgt gac ccc agc cct         1186
Thr Gly Ala Thr Cys Glu Leu Gly Ile Asp Glu Cys Asp Pro Ser Pro
300                 305                 310                 315 tgt aag aac gga ggg agc tgc acg gat ctc gag aac agc tac tcc tgt         1234
Cys Lys Asn Gly Gly Ser Cys Thr Asp Leu Glu Asn Ser Tyr Ser Cys
                320                 325                 330 acc tgc cca ccc ggc ttc tac ggc aaa atc tgt gaa ttg agt gcc atg         1282
Thr Cys Pro Pro Gly Phe Tyr Gly Lys Ile Cys Glu Leu Ser Ala Met
            335                 340                 345 acc tgt gcg gac ggc cct tgc ttt aac ggg ggt cgg tgc tca gac agc         1330
Thr Cys Ala Asp Gly Pro Cys Phe Asn Gly Gly Arg Cys Ser Asp Ser
        350                 355                 360 ccc gat gga ggg tac agc tgc cgc tgc ccc gtg ggc tac tcc ggc ttc         1378
Pro Asp Gly Gly Tyr Ser Cys Arg Cys Pro Val Gly Tyr Ser Gly Phe
365                 370                 375 aac tgt gag aag aaa att gac tac tgc agc tct tca ccc tgt tct aat         1426
Asn Cys Glu Lys Lys Ile Asp Tyr Cys Ser Ser Ser Pro Cys Ser Asn
380                 385                 390                 395 ggt gcc aag tgt gtg gac ctc ggt gat gcc tac ctg tgc cgc tgc cag         1474
Gly Ala Lys Cys Val Asp Leu Gly Asp Ala Tyr Leu Cys Arg Cys Gln
                400                 405                 410
```

| | |
|---|---|
| gcc ggc ttc tcg ggg agg cac tgt gac gac aac gtg gac gac tgc gcc<br>Ala Gly Phe Ser Gly Arg His Cys Asp Asp Asn Val Asp Asp Cys Ala<br>415                      420                    425 | 1522 |
| tcc tcc ccg tgc gcc aac ggg ggc acc tgc cgg gat ggc gtg aac gac<br>Ser Ser Pro Cys Ala Asn Gly Gly Thr Cys Arg Asp Gly Val Asn Asp<br>        430                    435                    440 | 1570 |
| ttc tcc tgc acc tgc ccg cct ggc tac acg ggc agg aac tgc agt gcc<br>Phe Ser Cys Thr Cys Pro Pro Gly Tyr Thr Gly Arg Asn Cys Ser Ala<br>445                      450                    455 | 1618 |
| ccc gtc agc agg tgc gag cac gca ccc tgc cac aat ggg gcc acc tgc<br>Pro Val Ser Arg Cys Glu His Ala Pro Cys His Asn Gly Ala Thr Cys<br>460                      465                    470                    475 | 1666 |
| cac gag agg ggc cac cgc tat gtg tgc gag tgt gcc cga ggc tac ggg<br>His Glu Arg Gly His Arg Tyr Val Cys Glu Cys Ala Arg Gly Tyr Gly<br>                      480                    485                    490 | 1714 |
| ggt ccc aac tgc cag ttc ctg ctc ccc gag ctg ccc ccg ggc cca gcg<br>Gly Pro Asn Cys Gln Phe Leu Leu Pro Glu Leu Pro Pro Gly Pro Ala<br>        495                    500                    505 | 1762 |
| gtg gtg gac ctc act gag aag cta gag ggc cag ggc ggg cca ttc ccc<br>Val Val Asp Leu Thr Glu Lys Leu Glu Gly Gln Gly Gly Pro Phe Pro<br>510                      515                    520 | 1810 |
| tgg gtg gcc gtg tgc gcc ggg gtc atc ctt gtc ctc atg ctg ctg ctg<br>Trp Val Ala Val Cys Ala Gly Val Ile Leu Val Leu Met Leu Leu Leu<br>525                      530                    535 | 1858 |
| ggc tgt gcc gct gtg gtg gtc tgc gtc cgg ctg agg ctg cag aag cac<br>Gly Cys Ala Ala Val Val Val Cys Val Arg Leu Arg Leu Gln Lys His<br>540                      545                    550                    555 | 1906 |
| cgg ccc cca gcc gac ccc tgc cgg ggg gag acg gag acc atg aac aac<br>Arg Pro Pro Ala Asp Pro Cys Arg Gly Glu Thr Glu Thr Met Asn Asn<br>                    560                    565                    570 | 1954 |
| ctg gcc aac tgc cag cgt gag aag gac atc tca gtc agc atc atc ggg<br>Leu Ala Asn Cys Gln Arg Glu Lys Asp Ile Ser Val Ser Ile Ile Gly<br>575                      580                    585 | 2002 |
| gcc acg cag atc aag aac acc aac aag aag gcg gac ttc cac ggg gac<br>Ala Thr Gln Ile Lys Asn Thr Asn Lys Lys Ala Asp Phe His Gly Asp<br>        590                    595                    600 | 2050 |
| cac agc gcc gac aag aat ggc ttc aag gcc cgc tac cca gcg gtg gac<br>His Ser Ala Asp Lys Asn Gly Phe Lys Ala Arg Tyr Pro Ala Val Asp<br>605                      610                    615 | 2098 |
| tat aac ctc gtg cag gac ctc aag ggt gac gac acc gcc gtc agg gac<br>Tyr Asn Leu Val Gln Asp Leu Lys Gly Asp Asp Thr Ala Val Arg Asp<br>620                      625                    630                    635 | 2146 |
| gcg cac agc aag cgt gac acc aag tgc cag ccc cag ggc tcc tca ggg<br>Ala His Ser Lys Arg Asp Thr Lys Cys Gln Pro Gln Gly Ser Ser Gly<br>                    640                    645                    650 | 2194 |
| gag gag aag ggg acc ccg acc aca ctc agg ggt gga gaa gca tct gaa<br>Glu Glu Lys Gly Thr Pro Thr Thr Leu Arg Gly Gly Glu Ala Ser Glu<br>655                      660                    665 | 2242 |
| aga aaa agg ccg gac tcg ggc tgt tca act tca aaa gac acc aag tac<br>Arg Lys Arg Pro Asp Ser Gly Cys Ser Thr Ser Lys Asp Thr Lys Tyr<br>        670                    675                    680 | 2290 |
| cag tcg gtg tac gtc ata tcc gag gag aag gat gag tgc gtc ata gca<br>Gln Ser Val Tyr Val Ile Ser Glu Glu Lys Asp Glu Cys Val Ile Ala<br>685                      690                    695 | 2338 |
| act gag gtg taaaatggaa gtgagatggc aagactcccg tttctcttaa<br>Thr Glu Val<br>700 | 2387 |
| aataagtaaa attccaagga tatatgcccc aacgaatgct gctgaagagg agggaggcct | 2447 |
| cgtggactgc tgctgagaaa ccgagttcag accgagcagg ttctcctcct gaggtcctcg | 2507 |

```
acgcctgccg acagcctgtc gcggcccggc cgcctgcggc actgccttcc gtgacgtcgc    2567
cgttgcacta tggacagttg ctcttaagag aatatatatt taaatgggtg aactgaatta    2627
cgcataagaa gcatgcactg cctgagtgta tatttt                              2663
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 9

```
tgacggtggg cgaggagtgg                                                  20
```

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 10

```
gcagctgtac cctccatcgg                                                  20
```

<210> SEQ ID NO 11
<211> LENGTH: 716
<212> TYPE: DNA
<213> ORGANISM: Homo sapiens

<400> SEQUENCE: 11

```
tgacggtggg cgaggagtgg tcccaggacc tgcacagcag cggccgcacg gacctcaagt      60
actcctaccg cttcgtgtgt gacgaacact actacgagag gggctgctcc gttttctgcc    120
gtccccggga cgatgccttc ggccacttca cctgtgggga gcgtggggag aaagtgtgca    180
accctggctg gaaagggccc tactgcacag agccgatctg cctgcctgga tgtgatgagc    240
agcatggatt ttgtgacaaa ccaggggaat gcaagtgcag agtgggctgg cagggccggt    300
actgtgacga gtgtatccgc tatccaggct gtctccatgg cacctgccag cagccctggc    360
agtgcaactg ccaggaaggc tgggggggcc ttttctgcaa ccaggacctg aactactgca    420
cacaccataa gccctgcaag aatggagcca cctgcaccaa cacgggccag gggagctaca    480
cttgctcttg ccggcctggg tacacaggtg ccacctgcga gctgggatt gacgagtgtg    540 accccagccc ttgtaagaac ggagggagct gcacggatct cgagaacagc tactcctgta    600
cctgcccacc cggcttctac ggcaaaatct gtgaattgag tgccatgacc tgtgcggacg    660
gcccttgctt taacgggggt cggtgctcag acagccccga tggagggtac agctgc        716
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 12

```
ttgggcacca actccttcgc                                                  20
```

```
<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
taggctgttg gcaatattcc                                                    20

<210> SEQ ID NO 14
<211> LENGTH: 412
<212> TYPE: DNA
<213> ORGANISM: Homo sapiens

<400> SEQUENCE: 14
ttgggcacca actccttcgc tgtccgggac gacagtagcg gcggggggcg caaccctctc        60
caactgccct tcaatttcac ctggccgggt accttctcgc tcatcatcga agcttggcac       120
gcgccaggag acgacctgcg gccagaggcc ttgccaccag atgcactcat cagcaagatc       180
gccatccagg gctccctagc tgtgggtcag aactggttat tggatgagca aaccagcacc       240
ctcacaaggc tgcgctactc ttaccgggtc atctgcagtg acaactacta tggagacaac       300
tgctcccgcc tgtgcaagaa gcgcaatgac cacttcggcc actatgtgtg ccagccagat       360
ggcaacttgt cctgcctgcc cggttggact ggggaatatt gccaacagcc ta              412

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
cggcgacgcc cgagggatg gcggcagc                                            28

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 16
gaattccacc gcggtggagc tccaattcgc                                         30

<210> SEQ ID NO 17
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 17
tcagctgggc ggcaagccca cggggaac                                           28

<210> SEQ ID NO 18
<211> LENGTH: 33
<212> TYPE: DNA
<213> ORGANISM: Artificial Sequence
<220> FEATURE:
```

<223> OTHER INFORMATION: Description of Artificial Sequence: Synthetic
      DNA

<400> SEQUENCE: 18
gcggccgctt atcgataccg tcgacctcga ggg                          33

<210> SEQ ID NO 19
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 19
tcatttatca tcatcatctt tataatcgct gggcggcaag cccacgggga ac     52

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 20
aaaggatccg agggcggcaa gcccacgggg aactcg                       36

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 21
ttatacctcc gtggcaatga cacat                                   25

<210> SEQ ID NO 22
<211> LENGTH: 52
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 22
tcatttatca tcatcatctt tataatctac ctccgtggca atgacacatt ca     52

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
aaggatcccg agggtgtctg ctggaagcca ggctca                       36

<210> SEQ ID NO 24
<211> LENGTH: 33
<212> TYPE: DNA
<213> ORGANISM: Artificial Sequence
<220> FEATURE:
<223> OTHER INFORMATION: Description of Artificial Sequence: Synthetic -continued

```
            DNA

<400> SEQUENCE: 24
cctctagagt cgcggccgtc gcactcattt acc                                33

<210> SEQ ID NO 25
<211> LENGTH: 685
<212> TYPE: PRT
<213> ORGANISM: Homo sapiens

<400> SEQUENCE: 25
```

Met Ala Ala Ser Arg Ser Ala Ser Gly Trp Ala Leu Leu Leu
    -25              -20              -15

Val Ala Leu Trp Gln Gln Arg Ala Ala Gly Ser Gly Val Phe Gln Leu
-10              -5               -1  1                5

Gln Leu Gln Glu Phe Ile Asn Glu Arg Gly Val Leu Ala Ser Gly Arg
            10                  15                  20

Pro Cys Glu Pro Gly Cys Arg Thr Phe Phe Arg Val Cys Leu Lys His
        25                  30                  35

Phe Gln Ala Val Val Ser Pro Gly Pro Cys Thr Phe Gly Thr Val Ser
    40                  45                  50

Thr Pro Val Leu Gly Thr Asn Ser Phe Ala Val Arg Asp Asp Ser Ser
55                  60                  65                  70

Gly Gly Gly Arg Asn Pro Leu Gln Leu Pro Phe Asn Phe Thr Trp Pro
                75                  80                  85

Gly Thr Phe Ser Leu Ile Ile Glu Ala Trp His Ala Pro Gly Asp Asp
            90                  95                  100

Leu Arg Pro Glu Ala Leu Pro Pro Asp Ala Leu Ile Ser Lys Ile Ala
        105                 110                 115

Ile Gln Gly Ser Leu Ala Val Gly Gln Asn Trp Leu Leu Asp Glu Gln
    120                 125                 130

Thr Ser Thr Leu Thr Arg Leu Arg Tyr Ser Tyr Arg Val Ile Cys Ser
135                 140                 145                 150

Asp Asn Tyr Tyr Gly Asp Asn Cys Ser Arg Leu Cys Lys Lys Arg Asn
                155                 160                 165

Asp His Phe Gly His Tyr Val Cys Gln Pro Asp Gly Asn Leu Ser Cys
            170                 175                 180

Leu Pro Gly Trp Thr Gly Glu Tyr Cys Gln Gln Pro Ile Cys Leu Ser
        185                 190                 195

Gly Cys His Glu Gln Asn Gly Tyr Cys Ser Lys Pro Ala Glu Cys Leu
    200                 205                 210

Cys Arg Pro Gly Trp Gln Gly Arg Leu Cys Asn Glu Cys Ile Pro His
215                 220                 225                 230

Asn Gly Cys Arg His Gly Thr Cys Ser Thr Pro Trp Gln Cys Thr Cys
                235                 240                 245

Asp Glu Gly Trp Gly Gly Leu Phe Cys Asp Gln Asp Leu Asn Tyr Cys
            250                 255                 260

Thr His His Ser Pro Cys Lys Asn Gly Ala Thr Cys Ser Asn Ser Gly
        265                 270                 275

Gln Arg Ser Tyr Thr Cys Thr Cys Arg Pro Gly Tyr Thr Gly Val Asp
    280                 285                 290

Cys Glu Leu Glu Leu Ser Glu Cys Asp Ser Asn Pro Cys Arg Asn Gly
295                 300                 305                 310

Gly Ser Cys Lys Asp Gln Glu Asp Gly Tyr His Cys Leu Cys Pro Pro
                315                 320                 325

```
Gly Tyr Tyr Gly Leu His Cys Glu His Ser Thr Leu Ser Cys Ala Asp
            330                 335                 340

Ser Pro Cys Phe Asn Gly Gly Ser Cys Arg Glu Arg Asn Gln Gly Ala
            345                 350                 355

Asn Tyr Ala Cys Glu Cys Pro Pro Asn Phe Thr Gly Ser Asn Cys Glu
            360                 365                 370

Lys Lys Val Asp Arg Cys Thr Ser Asn Pro Cys Ala Asn Gly Gly Gln
375                 380                 385                 390

Cys Leu Asn Arg Gly Pro Ser Arg Met Cys Arg Cys Arg Pro Gly Phe
                395                 400                 405

Thr Gly Thr Tyr Cys Glu Leu His Val Ser Asp Cys Ala Arg Asn Pro
            410                 415                 420

Cys Ala His Gly Gly Thr Cys His Asp Leu Glu Asn Gly Leu Met Cys
            425                 430                 435

Thr Cys Pro Ala Gly Phe Ser Gly Arg Arg Cys Glu Val Arg Thr Ser
            440                 445                 450

Ile Asp Ala Cys Ala Ser Ser Pro Cys Phe Asn Arg Ala Thr Cys Tyr
455                 460                 465                 470

Thr Asp Leu Ser Thr Asp Thr Phe Val Cys Asn Cys Pro Tyr Gly Phe
                475                 480                 485

Val Gly Ser Arg Cys Glu Phe Pro Val Gly Leu Pro Pro Ser Phe Pro
            490                 495                 500

Trp Val Ala Val Ser Leu Gly Val Gly Leu Ala Val Leu Leu Val Leu
            505                 510                 515

Leu Gly Met Val Ala Val Ala Val Arg Gln Leu Arg Leu Arg Arg Pro
520                 525                 530

Asp Asp Gly Ser Arg Glu Ala Met Asn Asn Leu Ser Asp Phe Gln Lys
535                 540                 545                 550

Asp Asn Leu Ile Pro Ala Ala Gln Leu Lys Asn Thr Asn Gln Lys Lys
                555                 560                 565

Glu Leu Glu Val Asp Cys Gly Leu Asp Lys Ser Asn Cys Gly Lys Gln
            570                 575                 580

Gln Asn His Thr Leu Asp Tyr Asn Leu Ala Pro Gly Pro Leu Gly Arg
            585                 590                 595

Gly Thr Met Pro Gly Lys Phe Pro His Ser Asp Lys Ser Leu Gly Glu
            600                 605                 610

Lys Ala Pro Leu Arg Leu His Ser Glu Lys Pro Glu Cys Arg Ile Ser
615                 620                 625                 630

Ala Ile Cys Ser Pro Arg Asp Ser Met Tyr Gln Ser Val Cys Leu Ile
                635                 640                 645

Ser Glu Glu Arg Asn Glu Cys Val Ile Ala Thr Glu Val
            650                 655

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      amino acid

<400> SEQUENCE: 26

Asp Tyr Lys Asp Asp Asp Asp Lys
 1               5
```

<210> SEQ ID NO 27
<211> LENGTH: 723
<212> TYPE: PRT
<213> ORGANISM: Homo sapiens

<400> SEQUENCE: 27

```
Met Gly Ser Arg Cys Ala Leu Ala Leu Ala Val Leu Ser Ala Leu Leu
    -20              -15                  -10
Cys Gln Val Trp Ser Ser Gly Val Phe Glu Leu Lys Leu Gln Glu Phe
 -5              -1   1               5                  10
Val Asn Lys Lys Gly Leu Leu Gly Asn Arg Asn Cys Cys Arg Gly Gly
             15                  20                  25
Ala Gly Pro Pro Pro Cys Ala Cys Arg Thr Phe Phe Arg Val Cys Leu
         30                  35                  40
Lys His Tyr Gln Ala Ser Val Ser Pro Glu Pro Cys Thr Tyr Gly
     45                  50                  55
Ser Ala Val Thr Pro Val Leu Gly Val Asp Ser Phe Ser Leu Pro Asp
 60                  65                  70                  75
Gly Gly Gly Ala Asp Ser Ala Phe Ser Asn Pro Ile Arg Phe Pro Phe
             80                  85                  90
Gly Phe Thr Trp Pro Gly Thr Phe Ser Leu Ile Ile Glu Ala Leu His
             95                 100                 105
Thr Asp Ser Pro Asp Asp Leu Ala Thr Glu Asn Pro Glu Arg Leu Ile
         110                 115                 120
Ser Arg Leu Ala Thr Gln Arg His Leu Thr Val Gly Glu Glu Trp Ser
     125                 130                 135
Gln Asp Leu His Ser Ser Gly Arg Thr Asp Leu Lys Tyr Ser Tyr Arg
140                 145                 150                 155
Phe Val Cys Asp Glu His Tyr Tyr Gly Glu Gly Cys Ser Val Phe Cys
                160                 165                 170
Arg Pro Arg Asp Asp Ala Phe Gly His Phe Thr Cys Gly Glu Arg Gly
             175                 180                 185
Glu Lys Val Cys Asn Pro Gly Trp Lys Gly Pro Tyr Cys Thr Glu Pro
         190                 195                 200
Ile Cys Leu Pro Gly Cys Asp Glu Gln His Gly Phe Cys Asp Lys Pro
     205                 210                 215
Gly Glu Cys Lys Cys Arg Val Gly Trp Gln Gly Arg Tyr Cys Asp Glu
220                 225                 230                 235
Cys Ile Arg Tyr Pro Gly Cys Leu His Gly Thr Cys Gln Gln Pro Trp
                240                 245                 250
Gln Cys Asn Cys Gln Glu Gly Trp Gly Gly Leu Phe Cys Asn Gln Asp
             255                 260                 265
Leu Asn Tyr Cys Thr His His Lys Pro Cys Lys Asn Gly Ala Thr Cys
         270                 275                 280
Thr Asn Thr Gly Gln Gly Ser Tyr Thr Cys Ser Cys Arg Pro Gly Tyr
     285                 290                 295
Thr Gly Ala Thr Cys Glu Leu Gly Ile Asp Glu Cys Asp Pro Ser Pro
300                 305                 310                 315
Cys Lys Asn Gly Gly Ser Cys Thr Asp Leu Glu Asn Ser Tyr Ser Cys
                320                 325                 330
Thr Cys Pro Pro Gly Phe Tyr Gly Lys Ile Cys Glu Leu Ser Ala Met
             335                 340                 345
Thr Cys Ala Asp Gly Pro Cys Phe Asn Gly Gly Arg Cys Ser Asp Ser
         350                 355                 360
```

```
Pro Asp Gly Gly Tyr Ser Cys Arg Cys Pro Val Gly Tyr Ser Gly Phe
    365                 370                 375
Asn Cys Glu Lys Lys Ile Asp Tyr Cys Ser Ser Ser Pro Cys Ser Asn
380                 385                 390                 395
Gly Ala Lys Cys Val Asp Leu Gly Asp Ala Tyr Leu Cys Arg Cys Gln
            400                 405                 410
Ala Gly Phe Ser Gly Arg His Cys Asp Asp Asn Val Asp Asp Cys Ala
            415                 420                 425
Ser Ser Pro Cys Ala Asn Gly Gly Thr Cys Arg Asp Gly Val Asn Asp
            430                 435                 440
Phe Ser Cys Thr Cys Pro Pro Gly Tyr Thr Gly Arg Asn Cys Ser Ala
    445                 450                 455
Pro Val Ser Arg Cys Glu His Ala Pro Cys His Asn Gly Ala Thr Cys
460                 465                 470                 475
His Glu Arg Gly His Arg Tyr Val Cys Glu Cys Ala Arg Gly Tyr Gly
                480                 485                 490
Gly Pro Asn Cys Gln Phe Leu Leu Pro Glu Leu Pro Pro Gly Pro Ala
            495                 500                 505
Val Val Asp Leu Thr Glu Lys Leu Glu Gly Gln Gly Gly Pro Phe Pro
            510                 515                 520
Trp Val Ala Val Cys Ala Gly Val Ile Leu Val Leu Met Leu Leu Leu
    525                 530                 535
Gly Cys Ala Ala Val Val Val Cys Val Arg Leu Arg Leu Gln Lys His
540                 545                 550                 555
Arg Pro Pro Ala Asp Pro Cys Arg Gly Glu Thr Glu Thr Met Asn Asn
                560                 565                 570
Leu Ala Asn Cys Gln Arg Glu Lys Asp Ile Ser Val Ser Ile Ile Gly
            575                 580                 585
Ala Thr Gln Ile Lys Asn Thr Asn Lys Lys Ala Asp Phe His Gly Asp
            590                 595                 600
His Ser Ala Asp Lys Asn Gly Phe Lys Ala Arg Tyr Pro Ala Val Asp
    605                 610                 615
Tyr Asn Leu Val Gln Asp Leu Lys Gly Asp Asp Thr Ala Val Arg Asp
620                 625                 630                 635
Ala His Ser Lys Arg Asp Thr Lys Cys Gln Pro Gln Gly Ser Ser Gly
                640                 645                 650
Glu Glu Lys Gly Thr Pro Thr Thr Leu Arg Gly Gly Glu Ala Ser Glu
            655                 660                 665
Arg Lys Arg Pro Asp Ser Gly Cys Ser Thr Ser Lys Asp Thr Lys Tyr
            670                 675                 680
Gln Ser Val Tyr Val Ile Ser Glu Glu Lys Asp Glu Cys Val Ile Ala
    685                 690                 695
Thr Glu Val
700
```

NUCLEIC ACIDS ENCODING DIFFERENTIATION INHIBITOR DELTA 2

This application is a divisional of 09/423,753, filed Dec. 12, 1999, now U.S. Pat. No. 6,664,098, which is a 371 of PCT/JP98/02104.

This invention relates to a novel bioactive substance.

BACKGROUND OF THE INVENTION

Human blood and lymph contain various types of cells and each cell plays important roles. For example, the erythrocyte carries oxygen; platelets have hemostatic action; and lymphocytes prevent from infection. These various cells originate from hematopoietic stem cells in the bone marrow. Recently, it has been clarified that the hematopoietic stem cells are differentiated to various blood cells, osteoclasts and mast cells by stimulation of various cytokines in vivo and environmental factors. In the cytokines, there have been found, for example, erythropoietin (EPO) for differentiation to erythrocytes; granulocyte colony-stimulating factor (G-CSF) for differentiation to leukocytes; and platelet growth factor (mpl ligand) for differentiation to megakaryocytes which is a platelet producing cells, and the former two have already been clinically applied.

The undifferentiated blood cells are generally classified into two groups consisting of blood precursor cells which are destined to differentiate to specific blood series and hematopoietic stem cells which have differentiation ability to all series and self-replication activity. The blood precursor cells can be identified by various colony assays, however identification method for the hematopoietic stem cells has not been established. In these cells, stem cell factor (SCF), interleukin-3 (IL-3), granulocyte-macrophage colony stimulating factor (GM-CSF), interleukin-6 (IL-6), interleukin-1 (IL-1), granulocyte colony stimulating factor (G-CSF) and oncostatin M have been reported to stimulate cell differentiation and proliferation.

Trials for expansion of hematopoietic stem cells in vitro have been examined in order to replace bone marrow transplantation for applying hematopoietic stem cell transplantation therapy or gene therapy. However, when the hematopoietic stem cells are cultured in the presence of the above mentioned cytokines, multi-differentiation activities and self-replication activities, which are originally in the position of the hematopoietic stem cells, gradually disappeared and are changed to the blood cell precursors which are only to differentiate to specific series after 5 weeks of cultivation, and multi-differentiation activity which is one of the specific features of the hematopoietic stem cells, is lost (Wagner et al. Blood 86, 512–523, 1995).

For proliferation of the blood precursor cells, single cytokine is not sufficient to effect, but synergistic action of several cytokines are important. Consequently, in order to proliferate the hematopoietic stem cells in maintaining with specific features of the hematopoietic stem cells, it is necessary to add cytokines which suppress differentiation together with the cytokines which proliferate and differentiate the undifferentiated blood cells. In general, many cytokines, which stimulate proliferation or differentiation of cells, are known, but small numbers of cytokines, which suppressed cell differentiation, are known. For example, leukemia inhibitory factor (LIF) has an action of proliferation of mouse embryonic stem cells without differentiation, but it has no action against the hematopoietic stem cells or blood precursor cells. Transforming growth factor (TGF—β) has suppressive action for proliferation against various cells, but no fixed actions against the hematopoietic stem cells or blood precursor cells.

Not only blood cells but also undifferentiated cells, especially stem cells are thought to be involved in tissue regeneration. These regeneration of tissues and proliferation of undifferentiated cells in each tissue can be applied in various ways by referring to the known reference (Katsutoshi Yoshizato, Regeneration—a mechanism of regeneration, 1996, Yodosha Publ. Co.).

Notch is a receptor type membrane protein, which involves in regulation of nerve cells differentiation found in *Drosophila*. Homologues of the Notch are found in various animal kinds exceeding to the invertebrate and vertebrate including nematode (Lin-12). *Xenopus laevis* (Xotch), mouse (Motch) or human (TAN-1).

Ligand of the Notch in *Drosophila* is known. These are *Drosophila* Delta (Delta) and *Drosophila* Serrate (Serrate). Notch ligand homologues are found in various animal kinds as similar to the Notch of receptors (Artavanis-Tsakonas et al., Science 268, 225–232, 1995).

Human Notch homologue, TAN-1 is found widely in the tissues in vivo (Ellisen et al., Cell 66, 649–661, 1991). Three Notch analogous molecules other than TAN-1 are reported (Artavanis-Tsakonas et al., Science 268, 225–232, 1995). Expression of TAN-1 was also observed in CD34 positive cells in blood cells by PCR (Polymerase Chain Reaction) (Milner et al., Blood 83, 2057–2062, 1994). However, in relation to humans, gene and amino acid sequences of human Delta and human Serrate, which are thought to be the Notch ligand, have not been reported as scientific reports in April 1997.

In *Drosophila* Notch, binding with the ligand was studied and investigated in details, and it was found that the Notch can be bound to the ligand with Ca++ at the binding region, which is a repeated amino acid sequence No. 11 and No. 12 in the amino acid sequence repeat of Epidermal Growth Factor (EGF) like repeating (Fehon et al., Cell 61, 523–534, 1990, Rebay et al., ibid. 67, 687–699, 1991 and International Publication WO 92/19734). EGF-like repeated sequences are conserved in Notch homologues of the other species. Consequently, the same mechanism in binding with ligand is estimated. An amino acid sequence which is called as DSL (Delta-Serrate-Lag-2) near the amino acid terminal, and EGF-like repeated sequence as like in the receptor are conserved in the ligand (Artavanis-Tsakonas et al., Science 268, 225–232, 1995).

EGF-like sequence has been found in thrombomodulin (Jackman et al., Proc. Natl. Acad. Sci. USA 83, 8834–8838, 1986), low density lipoprotein (LDL) receptor (Russell et al., Cell 37, 577–585, 1984), and blood coagulating factor (Furie et al., Cell 53, 505–518, 1988), and is thought to play important roles in extracellular coagulation and adhesion.

Recently, the vertebrate homologues of the cloned *Drosophila* Delta were found in chicken (C-Delta-1) and *Xenopus laevis* (X-Delta-1), and it has reported that X-Delta-1 had acted through Xotch in the generation of the protoneuron (Henrique et al., Nature 375, 787–790, 1995 and Chitnis et al., ibid. 375, 761–766,1995). Vertebrate homologue of *Drosophila* Serrate was found in rat as rat Jagged (Jagged) (Lindsell et al., Cell 80, 909–917, 1995). According to the Lindsell et al., mRNA of the rat Jagged is detected in the spinal cord of fetal rats. As a result of cocultivation of a myoblast cell line that is forced excess expressed rat Notch with a rat Jagged expression cell line, suppression of differentiation of the myoblast cell line is found. However, the rat Jagged has no action against the myoblast cell line without forced expression of the rat Notch.

A hypothesis has been set up so that Notch and its ligand have an action of differential regulation not only for neuroblasts and myoblasts, but also for various undifferentiated cells, especially blood undifferentiated cells. However, as far as clinical applications in humans, prior known different species such as chicken or *Xenopus laevos* type Notch ligand have problems with species specificities and antigenicities. Consequently, obtaining prior unknown human Notch ligand is essentially required. The inventor suspected that a molecule having DSL domain and EGF-like domain which are common to Notch ligand molecules and a ligand of the human Notch (TAN-1 etc.), which is a human Delta homologue (hereinafter designates as human Delta) and human Serrate homologue (hereinafter designates as human Serrate), may be found. In addition, these findings may be a candidate for a drug useful for differential regulation of undifferentiated cells.

As a result, in the previous patent application, a gene cloning of three types of molecules including human Delta-1, human Serrate-1 and human Serrate-2 molecules as the human Notch ligand molecules was made, and it was found that these molecules have an action on blood undifferentiated cells. (Refer to WO 97/19172 Differentiation-suppressive polypeptide and WO 98/02458 Differentiation-inhibitor). As for the human Notch ligand molecule, according to the recent report, partial gene and partial amino acid sequences of the human Delta-1 like molecule, which are, however, incomplete with respect to the specification and disclosure of the full-length sequence, have been disclosed in the International Publication WO 97/01571. Further, WO 96/27610 discloses total length gene and total length amino acid sequences of human Serrate-1 (humanJagged-1). Also, WO 96/27610 discloses partial length gene and partial length amino acid sequences of human Serate-2 (human Jagged-2). This gene sequence might have erroneous sequences and this gene sequence generates frame shift, which results completely different amino acid sequence of our WO 98/02458, Differentiation-inhibitor. In addition, the said prior arts did not disclose gene cloning of amino terminals. Consequently, the gene sequences and amino acid sequences are incomplete. As a result of searching the gene sequence database, Genebank Release 98 (December 1996), there are four entries about human Serrate-1, i.e. Registered No. HSU61276, HSU3936, HSU77720 and HSU77914, however no other human Notch ligand molecules are found in the said database.

The present invention elucidates the gene sequence and amino acid sequence of novel Notch ligand molecules. Novel Notch ligand molecules and novel therapeutic uses for these molecules are also provided.

In order to search novel human Notch ligands, cross hybridization using the human Delta-1 gene was performed.

To obtain the human Delta-1 gene, methods used in the referential examples 1 and 2, and WO 97/19172 can be applied. Transformed cells, in which a vector pUCDL-1 containing cDNA coding total amino acid sequence of human Delta-1, i.e. DNA containing sequence from No. 179 to No. 2347 in SEQ ID NO: 8, is inserted into *E. coli* JM109, have been deposited in the National Institute of Bioscience and Human-Technology, Agency of Industrial Science and Technology, Ministry of International Trade and Industry, in Higashi 1-1-3, Tsukuba, Ibaragi-ken, Japan as permanent culture collection *E. coli:* JM109-pUCDL-1F. Date of deposition was Oct. 28, 1996 as deposition No. FERM BP-5728.

Various lengths of partial genes of this human Delta-1 gene were prepared. Using these partial lengths of genes as probes, numerous cDNA libraries were screened under various hybridization conditions to determine novel Notch ligands by cross hybridization methods.

As a result of extensive studies, the isolation of cDNA coding amino acid sequences of novel human Delta-2 have been achieved, a novel molecule having DSL domain common to Notch ligand molecules from human fetal lung cDNA library, and have prepared the expression systems of protein having various forms using the cDNA. Also we have established purification methods of the proteins which were purified and isolated.

Amino acid sequences of novel human Delta-2 are shown in the sequence listings, SEQ ID NO: 1–3. DNA sequence coding these sequences is shown in the sequence listing, SEQ ID NO: 4.

Physiological actions of the these prepared proteins were searched by using many types of cells, for example nerve undifferentiated cells, preadipocytes, hepatocytes, myoblasts, skin undifferentiated cells, blood undifferentiated cells and immune undifferentiated cells. As a result, it has been found that novel human Delta-2 had a differentiation-suppressive action against undifferentiated blood cells, and had a physiological action to maintain an undifferentiated state. Further, it has been found that the molecule has growth suppressive action against vascular endothelial cells.

No significant toxic actions were noted in the toxicity studies on mice, and useful pharmaceutical effects were suggested. Consequently, the pharmaceutical preparations containing the molecule of the present invention, medium containing the molecule of the present invention, and the device immobilized with the molecule of the present invention are novel drugs and medical materials which can maintain the blood undifferentiated cells in the undifferentiated condition. Antibody against human Delta-2 is prepared by using antigen of the said human Delta-2, and purification method of the said antibodies is established. The present invention has completed accordingly.

The present invention relates to a polypeptide comprising at least amino acid sequence of SEQ ID NO: 1 of the sequence listing, a polypeptide comprising at least amino acid sequence of SEQ ID NO: 2 of the sequence listing, and a polypeptide comprising at least amino acid sequence of SEQ ID NO: 3 of the sequence listing. The present invention also relates to the said polypeptides having differentiation suppressive action against undifferentiated cells, the said polypeptides in which the undifferentiated cells are undifferentiated cells except for those of brain and nervous system or muscular system, the said polypeptides in which the undifferentiated cells are undifferentiated blood cells, and the said polypeptides acting on vascular cells. The present invention also relates to a pharmaceutical composition comprising the said polypeptides, and the said pharmaceutical composition having differentiation suppressive action against cells, the said pharmaceutical composition in which the cells are undifferentiated blood cells, and the said pharmaceutical composition having regulatory action against vascular cells. The present invention further relates to a cell culture medium comprising the said polypeptides, the cell culture medium in which the cell is undifferentiated blood cell, and a material having immobilized thereto the polypeptide. Further, the present invention relates to a method for culturing cells using the cell culture medium or the material, and the method in which the cells are undifferentiated blood cells.

The present invention further relates to a DNA coding at least an amino acid sequence of the sequence listing, SEQ ID NO: 1, said DNA coding at least an amino acid sequence of the sequence listing, SEQ ID NO: 2, the DNA coding at least an amino acid sequence of the sequence listing, SEQ ID NO: 3, the DNA having a base sequence from 355 to 927 of the sequence listing, SEQ ID NO: 4, the DNA having base sequence from 355 to 1854 of the sequence listing, SEQ ID NO: 4 and the DNA having base sequence from 355 to 2331 of the sequence listing SEQ ID NO: 4. The present invention still further relates to a recombinant DNA comprising a DNA selected from the group consisting of the DNAs having ligated to a vector DNA which can express said DNA in the host cell, a cell transformed by the recombinant DNA, a method for culturing human cells with the said cells, and a process for production of said polypeptide by culturing the said cells and isolating the compound produced in the cultured mass. The present invention still more further relates to an antibody specifically recognizing a polypeptide having an amino acid sequence of the sequence listing, SEQ ID NO: 3.

DETAILED DESCRIPTION OF THE INVENTION

Preparation of cDNA necessary for gene manipulation, expression analysis by Northern blotting, screening by hybridization, preparation of recombinant DNA, determination of DNA base sequence and preparation of cDNA library, all of which are series of molecular biological experiments, can be performed according to a description of the conventional textbook for the experiments. The above conventional textbook of the experiments is, for example, Maniatis et al. ed. Molecular Cloning, A laboratory manual, 1989, Eds., Sambrook, J., Fritsch, E. F. and Maniatis, T., Cold Spring Harbor Laboratory Press.

A polypeptide of the present invention has at least polypeptides in the sequence listing SEQ ID NO: 1–3. A mutant and allele, which naturally occur in the nature, are included in the polypeptide of the present invention unless the polypeptides of the sequence listing, SEQ ID NO: 1–3 loses their properties. Modification and substitution of amino acids are described in details in the patent application by the name of Benntt et al. (National Unexam. Publ. WO 96/2645) and can be prepared according to the description thereof.

A DNA sequence coding polypeptides of the sequence listing, SEQ ID NO: 1–3 is shown in the sequence listing, SEQ ID NO: 4, together with their amino acid sequences. In these DNA sequences, even if amino acid level mutation is not generated, naturally isolated chromosomal DNA or cDNA thereof may have a possibility to mutate in the DNA base sequence as a result of degeneracy of genetic code without changing amino acid sequence coded by the DNA. A 5'-untranslated region and 3'-untranslated region do not involve in amino acid sequence determination of the polypeptide, so DNA sequences of these regions are easily mutated. The base sequence obtained by these regeneracies of genetic codes is included in the DNA of the present invention.

Undifferentiated cells in the present invention are defined as cells, which can growth by specific stimulation, and cells, which can be differentiated to the cells having specific functions as a result of the specific stimulation. These include undifferentiated cells of the skin tissues, undifferentiated cells of the brain and nervous systems, undifferentiated cells of the muscular systems and undifferentiated cells of the blood cells. These cells include the cell of self-replication activity which is called as stem cells, and the cell having an ability to generate the cells of these lines. The differentiation-suppressive action means suppressive action for autonomous or heteronomous differentiation of the undifferentiated cells, and is an action for maintaining undifferentiated condition. The brain and nervous undifferentiated cells can be defined as cells having ability to differentiate to the cells of the brain or nerve having specific functions by specific stimulation. The undifferentiated cells of the muscular systems can be defined as cells having ability to differentiate to the muscular cells having specific functions by specific stimulation. The blood undifferentiated cells in the present invention can be defined as cell groups consisting of the blood precursor cells which are differentiated to the specific blood series identified by blood colony assay, and hematopoietic stem cells having differentiation to every series and self-replication activities. Further, in the present invention, vascular cells is defined as general nomination for cells constituting blood vessels, in which vascular endothelial cells is major constituting cells.

The amino acid sequence in the sequence listing, SEQ ID NO: 1 is a sequence of the active center of the novel human Delta-2 of the present invention, from which the signal peptide is deleted, i.e. amino acid sequence from the amino terminal to DSL domain, and corresponds to an amino acid No. 1 to 191 in SEQ ID NO: 3 of the matured full length aminoacid sequence of the novel human Delta-2 of the present invention.

The amino acid sequence in SEQ ID NO: 2 is amino acid sequence of extracellular domain of the novel human Delta-2 of the present invention, from which the signal peptide is deleted, and corresponds to an amino acid No. 1 to 500 in SEQ ID NO: 3 of the matured full length amino acid sequence of the novel human Delta-2 of the present invention.

The amino acid sequence of SEQ ID NO: 3 is the matured full length amino acid sequence of the novel human Delta-2 of the present invention.

The sequence of SEQ ID NO: 4 is cDNA sequence and total amino acid sequence of the novel human Delta-2 of the present invention, which corresponds to the coding region of the said cDNA.

The sequence of SEQ ID NO: 5 is DNA sequence which codes FLAG peptide and amino acid sequence of FLAG peptide used in the present invention.

The sequences of SEQ ID NOs: 6 and 7 are DNA sequences of primers used in referential example 1.

The sequence of SEQ ID NO: 8 is the cDNA sequence and total amino acid sequence of human Delta-1 used in the present invention.

The sequences of SEQ ID NOs: 9, 10, 12 and 13 are DNA sequences of primers used in example 1.

The sequence of SEQ ID NO: 11 is a DNA sequence of a probe used in example 1.

The sequence of SEQ ID NO: 14 is a DNA sequence of a probe used in examples 1 and 2.

The sequences of SEQ ID NOs: 15 to NO: 24 are DNA sequences of primers used in example 3.

The left and right ends of the amino acid sequences in the sequence listings indicate amino terminal (hereinafter designates as N-terminal) and carboxyl terminal (hereinafter designates as C-terminal), respectively, and the left and right ends of the nucleotide sequences are 5'-terminal and 3'-terminal, respectively.

Cloning of unknown human Notch ligand gene can be performed by the following method. During the evolution of the organisms, a part of amino acids sequences and gene sequences of the human Notch ligand is conserved. Cloning can be theoretically possible by using the other Notch legand molecule as a probe. However, in such the cross hybridization, there are many problems, for example, what part is preferable for the probe or how to set up condition for hybridization, and are not so simple. Further, since the cross hybridization process tends to make cloning many numbers of similar genes simultaneously, it takes much times for gene sequence analysis, consequently identification of the objective molecules from the cloned genes is quite difficult.

More than 10 gene fragments have been prepared from the human Delta-1 gene. By using said probes, screenings of cDNA libraries which originate from more than ten different organs were performed under numerous hybridization conditions and washing conditions. A novel Delta like molecule has been sought after.

In the plaque hybridization, clones can be obtained by isotope labeling and non-isotope labeling with the probe. Isotope labeling can be performed by, for example, terminal labeling by using [32P]γ-ATP and T4 polynucleotide kinase, or other labeling methods such as nick translation or primer extension method can be applied.

As a result, in example 1, a screening of a human fetal lung cDNA library was prepared using a partial gene of the full length gene of the human Delta-1 as shown in SEQ ID NO: 8 in the sequence listing, i.e. gene sequence shown in SEQ ID NO: 11 in the sequence listing, as a probe. As a result of the first screening, about 120 positive plaques were isolated, and in the second screening, about 80 positive plaques were cloned, then gene sequences of these clones were determined. Most of these cloned genes were the human Delta-1 gene used as a probe. Among them, five clones were found as the novel human Delta-2 gene, which is similar to the human Delta-1 gene, and the objective novel Notch ligand molecule was found. these cloned genes were the human Delta-1 gene used as a probe. Among them, five clones were found as the novel human Delta-2 gene, which is similar to the human Delta-1 gene, and objective novel Notch ligand molecule was found.

Among the above five clones, since there were no signal sequence and no amino terminal sequence, a new probe having a gene sequence as shown in SEQ ID NO: 14 was prepared in order to obtain the full length gene. Further, a screening of said human fetal lung cDNA library was repeated with this probe. As a result, cloning of the cDNA coding for the full length of gene was accomplished.

This sequence was compared with the database (Genbank Release 89, December 1996), and found that these were novel sequence.

Examples of plasmids integrated with cDNA are, for (example, other than pBluescript KS described in example 1, *E. coli* originated pBR322, pUC18, pUC19, pUC118 and pUC119 (Takara Shuzo Co. Japan), but the other plasmids can be used, if they can replicate and proliferate in the host cells. Examples of phage vectors integrated with cDNA are, for example, λgt10 and λgt11, but the other vectors can be used, if they can growth in the host cells. The thus obtained plasmids are transduced into suitable host cells such as genus *Escherichia* and genus *Bacillus* using calcium chloride method. Examples of the above genus *Escherichia* are *Escherichia coli* K12HB101, MC1061, LE392 and JM109. Example of the above genus *Bacillus* is *Bacillus subtilis* MI114. Phage vector can be introduced into the proliferated *E. coli* by the in vitro packaging method (Enquist and Sternberg, Meth. Enzymol., 68, 281-, 1979).

The said amino acid sequence was analyzed hydrophobic part and hydrophilic part from amino acid sequence according to the method of Kyte-Doolittle (J. Mol. Biol. 151: 105, 1982). As a result, the novel human Delta-2 of the present invention is expressed on cells as cell membrane protein having one transmembrane domain.

According to an analysis of the amino acid sequence of the novel human Delta-2, an amino acid sequence of a precursor of the novel human Delta-2 consists of a 685 amino acid residue shown in the sequence listing, SEQ ID NO: 4, and the signal peptide domain is estimated to correspond to the amino acid sequence of 26 amino acids residue from No. −26 methionine to No. −1 glycine of the sequence listing; extracellular domain: 500 amino acids residue from No. 1 serine to No. 500 serine; transmembrane domain: 26 amino acids residue from No. 501 phenylalanine to No. 526 valine; and intracellular domain: 133 amino acids residue from No. 527 arginine to No. 659 valine. The domain construction is estimated from the amino acid sequences, and an actual presence forms on the cells. Furthermore, a solution may be possible that differs from the above structure, and structural amino acid sequence of each domain hereinabove as defined by possibly changing 5 to 10 amino acids of the sequence.

N-terminal amino acid sequence of the human Delta-2 polypeptide, which is expressed in COS-7 cells, produced and purified as described in example 5, has at least the amino acid sequence started from No, 1 serine in the sequence listing, SEQ ID NO: 2. Similarly, identical N-terminal can be expected, if the said peptide is expressed in the other animal cells.

According to a comparison in the full length amino acid sequence of the novel human Delta-2 of the present invention with other Notch ligand molecules, which has been reported by April 1997, the homology with human Delta-1 (amino acid sequence of SEQ ID NO: 8 in the sequence listing) as a molecule originated from human is 48.5%; with Serrate-1 (Genbank HSU61276 and HSU73939) is 40.3%; and with human Serrate-2 (Japanese Patent Appln. No. 8-18622, Differentiation-suppressive polypeptide in the name of the present inventors) is 42,7%. The homologies with Delta of other vertebrates are: mouse Delta-1 (D111, Genbank MMDELTA1) 48.7%: flog Delta-1 (Genbank XELXDEL) 47.0%; flog Delta-2 (Genbank XLU70843) 49.7%, and chicken Delta-1 (Genbank GGU26590) 47.9%

As the result, the human Delta-2 of the present invention is a novel molecule, which has never been reported in humans or in other biological homologues, and is a novel substance having an amino acid sequence different from these substances, and is a novel substance which has been elucidated for the first time by the present inventor. Moreover, no polypeptide having the same amino acid sequence as the novel human Delta-2 has been found by a homology search in other organisms.

The homologues of Notch ligand have an evolutionary conserved common sequence, i.e. a DSL sequence and repeated EGF-like sequence. As a result of a comparison with the novel human Delta-2 and human Delta-1, these conserved amino acid sequences of the novel human Delta-2 are estimated.

Namely, DSL sequence corresponds to 43 amino acids residue from No. 149 cystine to No. 191 cystine of the amino acid sequence in the sequence listing, SEQ ID NO. 4. EGF-like sequence exists with 8 repeats wherein, in the amino acid sequence in the sequence listing, SEQ ID NO: 4, the first EGF-like sequence corresponds to the sequence from No. 196 cystine to No. 224 cystine: the second EGF-like sequence corresponds to the sequence from No. 227 cystine to No. 225 cystine; the third EGF-like sequence corresponds to the sequence from No. 262 to No. 295 cystine: the fourth EGF-like sequence corresponds to the sequence from No. 302 cysteine to No. 333 cysteine; the fifth EGF-like sequence corresponds to the sequence from No. 340 cysteine to No. 373 cysteine; the sixth EGF-like sequence corresponds to the sequence from No. 380 cysteine to No. 411 cysteine; the seventh EGF-like sequence corresponds to the sequence from No. 418 cysteine to No. 449 cysteine; and the eighth EGF-like sequence corresponds to the sequence from No. 458 cysteine to No. 491 cysteine.

A part of sugar chain attached is estimated from amino acid sequence of the novel human Delta-2 may be No. 82, 157, 179 and 367 asparagine residue in the sequence listing, SEQ ID NO: 4 as a possible binding site of N-glycoside bonding for N-acetyl-D-glucosamine. O-glycoside bond of N-acetyl-D-galactosamineis estimated to be a serine or threonine residue rich part. Protein bound with sugar chain is generally thought to be stable in vivo and to have strong physiological activity. Consequently, in the amino acid sequence of polypeptide having sequence of the sequence listing SEQ ID NO: 1, 2 or 3, polypeptides having N-glucoside or O-glucoside bond with sugar chain of N-acetyl-D-glucosamine or N-acetyl-D-galactosamine is included in the present invention. As shown in example 5, if the human Delta-2 of the present invention is expressed by gene inserted COS-7 cell, at least more than two forms are expressed due to attached sugar chain as the proteins having different molecular weight.

As a result of studies on binding of *Drosophila* Notch and its ligand, amino acid region necessary for binding with ligand of *Drosophila* Notch with the Notch is from N-terminal to DSL sequence of the matured protein, in which signal peptide is removed (International Publication WO 92/19734). Further, similarly, studies using Nematode by Fitzgerald and Greenwald (Development, 121, 4275–4282, 1995) clearly indicate that Notch ligand like molecule APX-1 required for Notch like receptor activation is sufficient from amino terminal to DSL domain in the full length sequence.

This fact indicates that a domain necessary for expression of ligand action of human Notch ligand molecule is at least the DSL domain, i.e. a domain containing amino acid sequence from No. 149 cycteine to No. 191 cycteine in the sequence listing, SEQ ID NO: 1, and a domain at least necessary for expression of ligand action of human Delta-2 is novel amino acid sequence shown in the sequence listing, SEQ ID NO: 1, further a domain at least necessary for expression of ligand action of human Delta-2 is novel amino acid sequence shown in the sequence listing, SEQ ID NO: 2.

As shown in example 2, mRNA of the human Delta-2 can be detected by using DNA coding a part or full of gene sequence in the sequence listing, SEQ ID NO: 4. For example, a method for detection of expression of these genes can be achieved by applying with hybridization or PCR by using complementary nucleic acids of above 12mer or above 16mer, preferably above 20mer having nucleic acid sequence of a part of swquence in the sequence listing, SEQ ID NO: 4, i.e. antisense DNA or antisense RNA, its methylated, methylphosphated, deaminated or thiophosphated derivatives. Using the same method, detection of homologues of the gene of other organisms such as mice or gene cloning can be achieved. Further cloning of genes in the genome including humans can be made. Using these genes cloned by such like methods, further detailed functions of the human Delta-2 can be clarified. For example, using the recent gene manipulation techniques, every methods including transgenic mouse, gene targeting mouse or double knockout mouse in which genes relating to the gene of the present invention are inactivated, can be applied. If abnormalities in the genome of the present gene are found, application to gene diagnosis and gene therapy can be made.

A transformant in which vector pBSDL-2, which contains cDNA coding total amino acid sequence of the novel human Delta-2 of the present invention, is transformed into *E. coli* JM109, has been deposited in the National Institute of Bioscience and Human-Technology, Agency of Industrial Science and Technology, Ministry of International Trade and Industry, of 1-1-3, Higashi, Tsukuba-shi, Ibaragi-ken, Japan, as *E. coli:* JM109-pBSDL-2. Date of deposit was May 9, 1997, and deposition No. is FBRM BP-5941.

Process for production of the novel human Delta-2 polypeptide can be performed, as shown in example 3, by using expression vector pcDNA 3. Production and purification of various forms of the novel human Delta-2 polypeptide using cDNA, which codes amino acid sequence of the novel human Delta-2 isolated by the above method are known in the references (Kriegler, Gene Transfer and Expression-A Laboratory Manual, Stockton Press, 1990 and Yokota et al. Biomanual Series 4, Gene Transfer and Expression and Analysis, Yodosha Co., 1994). A cDNA coding the amino acid sequence of the isolated said human Delta-2 is ligated to preferable expression vector and it is produced in the host cells of eukaryotic cells such as animal cells and insect cells or prokaryotic cells such as bacteria.

In the expression of the novel human Delta-2 of the present invention, DNA coding polypeptide of the present invention may have the translation initiation codon in 5'-terminal and translation termination codon in 3'-terminal. These translation initiation codon and translation termination codon can be added by using preferable synthetic DNA adapter. Further for expression of the said DNA, promoter is ligated in the upstream of the DNA sequence. Examples of vector are plasmid originated from the above *E. coli,* plasmid originated from *Bacillus,* plasmid originated from yeast or bacteriophage such as λ-phage and animal viruses such as retrovirus and vaccinia virus.

Examples of promoters used in the present invention are any promoters preferable for corresponding to the host cells used in gene expression.

In case that the host cell in the transformation is genus *Escherichia,* tac-promoter, trp-promoter and lac-promoter are preferable, and in case of host of genus *Bacillus,* SP01 promoter and SP02 promoter are preferable, and in case of host of yeast, PGK promoter, GAP promoter and ADH promoter are preferable.

In case that the host cell is animal cell, a promoter originated from SV40, promoter of retrovirus, metallothionein promoter and heat shock promoter can be applied.

Expression of the polypeptide of the present invention can be made by using only DNA coding the amino acid sequence of the sequence listing, SEQ ID NO: 1, 2 or 3. However, the protein added with specific function can be produced by using DNA, to which added cDNA coding the known antigen epitope for easier detection of the produced polypeptide or added cDNA coding the immunoglobulin Fc for forming multimer.

As shown in Example 3, we have prepared expression vectors, which express extracellular proteins of the novel human Delta-2, as follow:

1) DNA coding the amino acids from No. 1 to 500 in amino acid sequence in the sequence listing, SEQ ID NO: 2;

2) DNA coding chimera protein, to which added polypeptide having 8 amino acids, i.e. an amino acid sequence consisting of Asp Tyr Lys Asp Asp Asp Asp Lys (hereinafter designates FLAG sequence, an example of DNA sequence coding the same is shown in the sequence listing, SEQ ID NO: 5), in the C-terminal of the amino acids from No. 1 to 500 in amino acid sequence in the sequence listing, SEQ ID NO: 2; and 3) DNA coding chimera protein, to which added Fc sequence from the hinge region of human IgG1 in the C-terminal of the amino acids from No. 1 to 500 in amino acid sequence in the sequence listing, SEQ ID NO: 2, is ligated to each separately with the expression vector pcDNA 3 (INVITROGEN Corp., U.S.A.), then the expression vector expressing the extracellular region of the novel human Delta-2 is prepared.

The expression vector for expression of full length of the novel human Delta-2 can be prepared as follows:

4) DNA coding amino acids from No. 1 to 659 in the sequence listing, SEQ ID NO: 3 and 5) DNA coding chimera protein, to which added polypeptide having FLAG sequence in the C-terminal of amino acids from No. 1 to 659 in the sequence listing, SEQ ID NO: 3 are ligated individually with the expression vector pcDNA to prepare the expression vector, which can express full length of the novel human Delta-2.

The transformants are prepared by using these expression plasmids containing DNA coding the thus constructed said human Delta-2.

Examples of the host are genus *Escherichia*, genus *Bacillus*, yeast and animal cells. Examples of animal cells are simian cell COS-7 and Vero, Chinese hamster cell CHO and silk worm cell SF9.

As shown in Example 4, the expression vectors of the above 1)–5) are transduced individually; the novel human Delta-2 is expressed in COS-7 cell (obtainable from the Institute of Physical and Chemical Research, Cell Development Bank, RCB0539), and the transformants, which are transformed by these expression plasmids, can be obtained. Further, the novel human Delta-2 polypeptide can be produced by culturing the transformants under preferable culture condition in medium by known culture method.

As shown in Example 5, the novel human Delta-2 polypeptide can be isolated and purified from the above cultured mass, in general, by the following methods.

For extraction of the substance from cultured microbial cells or cells, microbial cells or cells are collected by known methods such as centrifugation after the cultivation, suspended in preferable buffer solution, disrupted the microbial cells or cells by means of ultrasonication, lysozyme and/or freeze-thawing and collected crude extract by centrifugation or filtration. The buffer solution may contain protein-denaturing agents such as urea and guanidine hydrochloride or surface active agents such as Triton-X. In case of secretion in the cultured solution, the cultured mass is separated by the known method such as centrifugation to separate from microbial cells or cells and the supernatant solution is collected.

The thus obtained novel human Delta-2, which is contained in the cell extracts or cell supernatants, can be purified by known protein purification methods. During the purification process, for confirmation of existence of the protein, in case of the fused proteins such as the above FLAG and human IgGFc, they can be detected by immunoassay using antibody against known antigen epitope and can be purified. In case of not to express as such the fused protein, the antibody in Example 6 can be used for detection.

Antibodies, which specifically recognize human Delta-2, can be prepared as shown in Example 6. Antibodies can be prepared by the methods described in the reference (Antibodies a laboratory manual, E. Harlow et al., Cold Spring Harbor Laboratory) or recombinant antibodies expressed in cells by using immunoglobulin genes isolated by gene cloning method. The thus prepared antibodies can be used for purification of the novel human Delta-2. The human Delta-2 can be detected and assayed by using antibodies which recognize specifically novel human Delta-2 as shown in Example 6, and can be used for diagnostic agents for diseases accompanied with abnormal differentiation of cells such as malignant tumors.

More useful purification method is the affinity chromatography using antibody. Antibodies used in this case are antibodies described in Example 6. For fused protein, antibodies against FLAG in the case of FLAG, and protein G or protein A in the case of human IgGFc as shown in Example 5.

Physiological functions of the thus purified human Delta-2 protein can be identified by various assay methods, for example, physiological activity assaying methods using cell lines and animals such as mice and rats, assay methods of intracellular signal transduction based on molecular biological means, binding with Notch receptor etc.

Actions for blood undifferentiated cells have been observed by using IgG1 chimera protein of novel human Delta-2. As a result, it has been found that, as shown in example 7, in undifferentiated umbilical cord derived blood cells, in which the CD34 positive cell fraction is concentrated, the novel human Delta-2 has suppressive action of colony forming action against blood undifferentiated cells, which show colony formation in the presence of cytokines.

Further as shown in example 8, it has been found that by evaluating LTC-IC (Long-term Culture-Initiating Cells), which are positioned from most undifferentiated blood stem cells in the human blood undifferentiated cells, after culturing the undifferentiated umbilical cord derived blood cells, in which the CD34 positive cell fraction is concentrated, in the presence of the human Delta-2 with various cytokines in serum-free medium, the human Delta-2 has an activity to maintain a number of LTC-IC. Further, example 9 shows that the human Delta-2 is Bound with human blood undifferentiated cells.

The results indicate that the human Delta-2 suppresses differentiation of blood undifferentiated cells, and this action is obviously effective for cells from blood stem cells to colony forming cells. These physiological actions are essential for in vitro proliferation of blood undifferentiated cells. Especially, cells cultured in the medium containing human Delta-2 are efficient in recovery of suppression of bone marrow after administration of antitumor agents, accordingly in vitro expansion of hemopoietic stem cells may be possible if other conditions would be completed. Further pharmaceuticals containing the polypeptide of the present invention have protective and reduced actions against the bone marrow suppressive action due to adverse effects of antitumor agents.

In these experiments, the LTC-IC maintaining activity and binding action for blood cells of the novel human Delta-2 of the present invention are stronger than those of the human Delta-1 (WO 97/19172), which has same action as shown by the present inventors.

As shown in example 9, IgG1 chimera protein of the human Delta-2 is bound with CD34 positive blood undifferentiated cells. By this binding activity, the polypeptide of the present invention can be used for isolation and detection of cells. Although the isolation method can be performed by a method using flow cytometer as described in example 9, a method using materials, to which polypeptide of the present invention is immobilized, as described in example 11 may be more convenient. Consequently, cell isolation method using polypeptide of the present invention is included in the present invention. Further, cell isolation method using a material, to which polypeptide of the present invention is immobilized, and device for cell isolation applied with the said isolation method is also includedin the present invention. Any cell isolation method using antibodies described in the references is applicable to these isolation devices and isolation methods. For example, Dynabeads of Dynal Corp., Norway, which is a method using combination of magnetic beads and antibodies, can be used.

Further, as shown in example 12, IgG1 chimera protein of the novel human Delta-2 of the present invention has suppressive action against proliferation of intravascular endothelial cells and has inhibitory action against vascularization. Consequently, the polypeptide of the present invention can be used as therapeutic agents for diseases and disease states, which may be cured by suppressing vascularization as proposed by Folkman and Klagsbrun (Science 235, 442–447, 1987). Concrete examples of use are described in the above reference, and are, for example, diseases including malignant tumors.

Suppressive action for differentiation of cells in the undifferentiated cells other than blood cells is expected and stimulating action for tissue regeneration can be expected.

In the pharmaceutical use, polypeptides of the present invention are lyophilized with adding preferable stabilizing agents such as human serum albumin, and are used in dissolved or suspended condition with distilled water for injection when it is in use. For example, preparation for injection or infusion at the concentration of 0.1–1000 μg/ml may be provided. A mixture of the compound of the present invention 1 mg/ml and human serum albumin 1 mg/ml divided in a vial could maintain activity of the said compound for long term. For culturing and activating cells in vitro, lyophilized preparation or liquid preparation of the polypeptide of the present invention are prepared and are added to the medium or immobilized in the vessel for culture. Toxicity of the polypeptide of the present invention was tested. Any polypeptide, 10 mg/kg was administered intraperitoneally in mice, but no death of mice was observed.

In vitro physiological activity of the polypeptide of the present invention can be evaluated by administering to disease model mice or its resembled disease rats or monkeys, and examining recovery of physical and physiological functions and abnormal findings. For example, in case of searching abnormality in relation to hemopoietic cells. bone marrow suppressive model mice are prepared by administering 5-FU series of antitumor agents, and bone marrow cell counts, peripheral blood cell counts and physiological functions are examined in the administered group or the non administered group of mice. Further, in case of searching in vitro cultivation and growth of hemopoietic undifferentiated cells including hemopoietic stem cells, the bone marrow cells of mice are cultured in the groups with or without addition of the compound of the present invention, and the cultured cells are transferred into the lethal dose irradiated mice. Result of recovery is observed with the indications of survival rate and variation of blood counts. These results can be extrapolated to the humans, and accordingly useful effective data for evaluation of the pharmacological activities of the compound of the present invention can be obtained.

Applications of the compound of the present invention for pharmaceuticals include diseases with abnormal differentiation of cells, for example leukemia and malignant tumors. These are cell therapy, which is performed by culturing human derived cells in vitro with maintaining their original functions or adding new functions, and a therapy, which is performed by regenerating without damaged the functions of the originally existed in the tissues by administering the compound of the present invention under the regeneration after tissue injury. Amount of administration may differ in the type of preparation and is ranged from 10 μg/kg to 10 mg/kg.

Further strong physiological activity can be achieved by expression of forming multimer of the polypeptide of the present invention.

Human Delta-2 having multimer structure can be produced by the method of expressing chimera protein with human IgG Fc region as described in the examples 3 and 4 and expressing the multimer having disulfide bond with hinge region of the antibody, or a method expressing chimera protein, in which antibody recognition region is expressed in the C-terminal or N-terminal, and reacting with the polypeptide containing extracellular part of the thus expressed said human Delta-2 and the antibody which recognize specifically the antibody recognition region in the C-terminal or N-terminal. In the other methods, a method, in which a fused protein with only the hinge region of the antibody is expressed and the dimer is formed by disulfide bond, can be mentioned. The multimer of human Delta-2 having higher specific activity than the dimer can be obtained. The said multimer is constructed by fused protein which is prepared for expressing the peptide in the C-terminal, N-terminal or other region. The protein is prepared in the form of forming disulfide bond without effecting in any activities of the other human Delta-2. The multimer structure can also be expressed by arranging one or more peptide, which is selected from polypeptides containing amino acids sequence of the sequence listing, SEQ ID NO: 1, 2 and 3, with genetic engineering method in series or in parallel. Other known methods for providing multimer structure having dimer or more can be applied. Accordingly, the present invention includes any polypeptides containing amino acid sequences described in the sequence listing, SEQ ID NO: 1, 2 and 3 in the form of dimer or more structure prepared by genetic engineering technique.

Further in the other method, multimerization method using chemical cross-linker can be mentioned. For example, dimethylsuberimidate dihydrochloride for cross-linking lysine residue, N-(γ-maleimidebutyryloxy) succinimide for cross-linking thiol group of cysteine residue and glutaraldehyde for cross-linking between amino groups can be mentioned. The multimer with dimer or more can be synthesized by applying these cross-linking reactions. Accordingly, the present invention includes any polypeptides containing amino acid sequences described in the sequence listing, SEQ ID NO: 1, 2 or 3 in the form of dimer or multimer structure prepared by chemical cross-linking agents.

In application of medical care in which cells are proliferated and activated in vitro and are returned to the body, human Delta-2 of the form hereinabove can be added directly in the medium, but immobilization can also be made. Immobilization method includes applying amino group or carboxyl group in the peptide, using suitable spacers or the above mentioned cross-linkers, and the polypeptide can be covalently bound to the culture vessels. In example 11, method for preparation of the immobilized material and their effect are illustrated. Accordingly, the present invention includes any polypeptides containing amino acid sequences described in the sequence listing, SEQ ID NO: 1, 2 or 3 in the form of existing on the solid surface.

Since the natural human Delta-2 is cell membrane proteins, differentiation suppressive action in example 7, 8 and 12 can be expressed by cocultivating with cells expressing these molecules and blood undifferentiated cells. Consequently, this invention includes a method for cocultivation of undiferentiated cells with transformed cells by using DNA coding amino acid sequence in the sequence listing, SEQ ID NO: 1, 2 or 3. An example is illustrated in example 10. Expressed cell may be simian COS-7 cell or mouse Balb 3T3 cells as shown in examples, but cells of human origin are preferable, and further expressed cells may be any of human in vivo blood cells and somatic cells rather than cell lines. Consequently, the polypeptide can be expressed in vivo by integrated into vectors for gene therapy. Examples of vectors for gene therapy are retrovirus vector, adenovirus vector or adeno-related virus vector.

This fact suggests that inhibition of binding of the polypeptide having amino acid sequence in the sequence listing, SEQ ID NO: 1, 2 or 3 to these receptors can be used for finding out molecules and compounds for stimulating cell differentiation. The methods include binding experiment using radio isotope, luciferase assay using transcriptional control factors, a down stream molecule of the Notch receptor, and simulation on the computer by X-ray structural analysis. Accordingly, the present invention includes a screening method for pharmaceuticals using polypeptide in the sequence listing, SEQ ID NO: 1, 2 or 3.

EMBODIMENTS OF THE INVENTION

Figure 1:
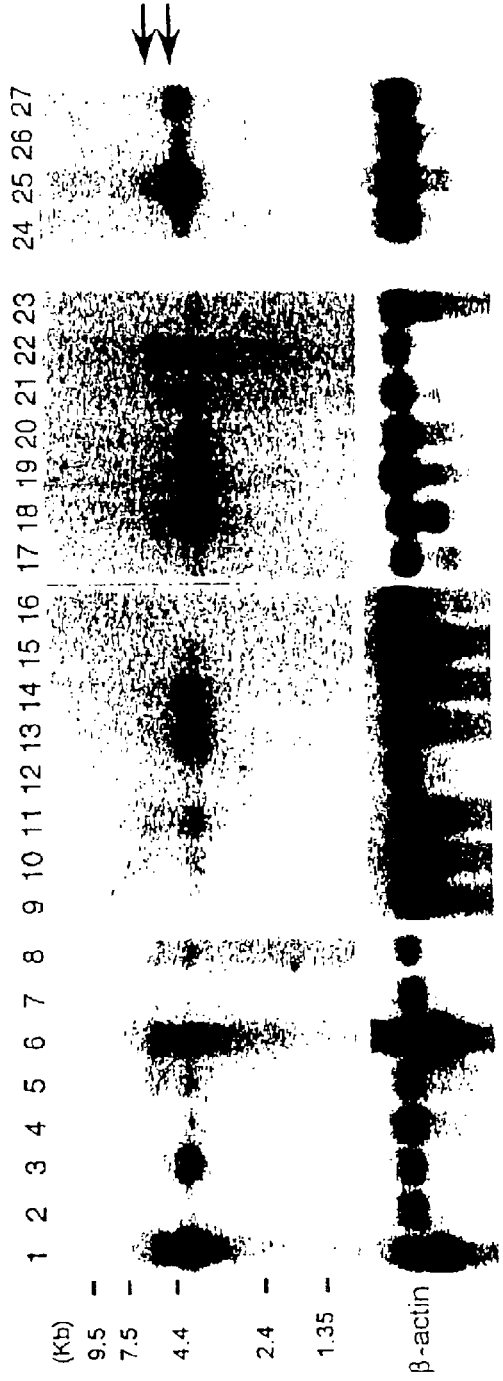
FIG. 1: Northern blotting analysis of expression of the human Delta-2 mRNA in human organs.

Following examples illustrate the embodiments of the present invention, but are not construed as limiting these examples.

REFERENTIAL EXAMPLE 1

Cloning of PCR Products Using Human Delta-1 Primer and Determination of Base Sequence Mixed primers corresponding to amino acid sequence conserved in C-Delta-1 and X-Delta-1, i.e. sense primer DLTS1 (sequence listing, SEQ ID NO: 6) and antisense primer DLTA2 (sequence listing, SEQ ID NO: 7), were used.

A synthetic oligonucleotide was prepared by using automatic DNA synthesizer with the principle of immobilized method. The automatic DNA synthesizer used was 391PCR-MATE of Applied Biosystems Inc., U.S.A. Nucleotide, carrier immobilized with 3'-nucleotide, solution and reagents are used according to the instructions by the same corporation. Oligonucleotide was isolated from the carrier after finishing the designated coupling reaction and treating the oligonucleotide carrier, from which protective group of 5'-terminal was removed, with concentrated liquid ammonia at room temperature for one hour. For removing the protective groups of nucleic acid and phosphoric acid, the reactant solution containing nucleic acid was allowed to stand in the concentrated ammonium solution in the sealed vial at 55° C. for over 14 hours. Each oligonucleotide, from which the carrier and protective groups were removed, was purified by using OPC cartridge of the Applied Biosystems Inc., and detritylated by using 2% trifluoroacetic acid. Primer was dissolved in deionized water to set final concentration of 100 pmol/μl for PCR after purification.

Amplification of these primers by PCR was performed as follows. Human fetal brain originated cDNA mixed solution (QUICK-Clone cDNA, CLONTECH Inc., U.S.A.) 1 μl was used. 10× buffer solution [500 mM KCl, 100 mM Tris-HCl (pH 8.3), 15 mM $MgCl_2$, 0.01% gelatin] 5 μl, dNTP mixture (Takara Shuzo Co., Japan) 4 μl, sense primer DLTS1 (100 pmol/μl) 5 μl which was specific to the above vertebrates and antisense primer DLTA2 (100 pmol/μl) 5 μl and TaqDNA polymerase (AmpliTaq, Takara Shuzo Co., Japan, 5 U/μl) 0.2 μl were added thereto, and finally deionized water was added to set up total 50 μl. PCR was performed by 5 cycles of a cycle consisting of treatment at 95° C. for 45 seconds, at 42° C. for 45 seconds and 72° C. for 2 minutes, further 35 cycles of a cycle consisting of treatment at 95° C. for 45 seconds, at 50° C. for 45 seconds and 72° C. for 2 minutes, and finally allowed to stand at 72° C. for 7 minutes. A part of the PCR products was subjected to 2% agarose gel electrophoresis, stained with ethidium bromide (Nippon Gene Co., Japan). and observed under ultraviolet light to confirm amplification of about 400 bp DNA.

Total amount of PCR product was subjected to electrophoresis with 2% agarose gel prepared by low melting point agarose (GIBCO BRL Inc., U.S.A.), stained by ethidium bromide, cutting out about 400 bp bands of PCR products by the Delta primer under the UV light, adding distilled water of the same volume of the gel, heating at 65° C. for 10 minutes, and completely dissolving the gel. The dissolved gel was centrifuged at 15000 rpm for 5 minutes to separate supernatant solution after adding equal volume of TE saturated phenol (Nippon Gene Co., Japan) and the same separation operation was performed after adding TE saturated phenol:chloroform (1:1) solution and chloroform. DNA was recovered from the final solution by ethanol precipitation.

A vector, pCRII vector (Invitorogen Inc., U.S.A., hereinafter designates as pCRII) was used. The vector and the above DNA in molar ratio of 1:3 were mixed and the DNA was ligated into the vector by using T4 DNA ligase (Invitorogen Inc., U.S.A.). The pCRII, to which the DNA was integrated, was subjected to gene transduction into E. coli one shot competent cells (Invitorogen Inc., U.S.A.) and was spread on the semi-solid medium plate of L-Broth (Takara Shuzo Co., Japan) containing ampicillin (Sigma Corp., U.S.A.) 50 μg/ml and allowed to stand at 37° C. for about 12 hours. The appeared colonies were randomly selected, inoculated in the L-Broth liquid medium 2 ml containing same concentration of ampicillin and shake cultured at 37° C. for about 18 hours. The cultured bacterial cells were recovered and the plasmid was separated by using Wizard Miniprep (Promega Inc., U.S.A.) according to the attached explanation sheet. The plasmid was digested by restriction enzyme EcoRI. Integration of the said PCR product was confirmed by incision of about 400 bp DNA. Base sequence of the incorporated DNA in the confirmed clone was determined by the fluorescent DNA sequencer (Model 373S. Applied System Inc., U.S.A.).

REFERENTIAL EXAMPLE 2

Cloning of Full Length Human Delta-1 and Its Analysis

A screening of clones having full length cDNA was performed by hybridization from human placenta origin cDNA library (inserted cDNA in λgt-11, CLONTECH Inc., U.S.A.) in plaques corresponding to $1\times10^6$ plaques. Generated plaques were transferred onto nylon filter (HybondN+: Amersham Inc., U.S.A.). The transcribed nylon filter was subjected to alkaline treatment [allow to stand for 7 minutes on a filter paper permeated with a mixture of 1.5 M NaCl and 0.5 M NaOH], followed by twice neutralizing treatments [allow to stand for 3 minutes on the filter paper permeated with a mixture of 1.5 M NaCl, 0.5 M Tris-HCl (pH 7.2) and 1 mM EDTA]. Subsequently, the filter was shaken for 5 minutes in the 2-fold concentrated SSPE solution [0.36 M NaCl, 0.02 M sodium phosphate (pH 7.7) and 2 mM EDTA], washed and air-dried. Then the nylon filter was allowed to stand for 20 minutes on the filter paper, which was permeated with 0.4 M NaOH, and was shaken for 5 minutes and washed with 5-fold concentrated SSPE solution, and was then again air-dried. Screening was conducted in the human Delta-1 probe labeled with radioisotope $^{32}P$ using these filters.

DNA probe prepared in referential Example 1 was labeled with $^{32}P$ as follows. A DNA fragment was cut out by EcoRI from pCRII, inserted a purified PCR product (about 400 bp) by human Delta-1 primer and determined gene sequence, and was isolated from low melting point agarose gel. The thus obtained DNA fragment was labeled by DNA labeling kit (Megaprime DNA labeling system: Amersham, U.S.A.). The primer solution 5 µl and deionized water were added to the DNA 25 ng to set up total volume of 33 µl, which was treated for 5 minutes in boiling water bath. Reaction buffer solution 10 µl containing dNTP, α-$^{32}$P-dCTP 5 µl and T4 DNA polynucleotide kinase solution 2 µl were added thereto, treated at 37° C. for 10 minutes in water bath. Subsequently, the mixture was purified by Sephadex column (Quick Spin Column Sephadex G-50: Boehringer Mannheim Inc., Germany), then treated for 5 minutes in boiling water bath and ice-cooled for 2 minutes for use.

Hybridization was performed as follows. The prepared filter hereinabove was immersed into the prehybridization solution consisting of SSPE solution, a final concentration of each component of which is set at 5-fold concentration, 5-fold concentration of Denhardt's solution (Wako Pure Chemicals, Japan), 0.5% SDS (sodium dodecyl sulfate, Wako Pure Chemicals, Japan) and salmon sperm DNA (Sigma, U.S.A.) 10 µg/ml denatured by boiling water, and shaken at 65° C. for 2 hours, then the filter was immersed into the hybridization solution of the same composition of the above prehybridization solution containing $^{32}$P-labeled probe by the above described method and shaken at 65° C. for 16 hours to perform hybridization.

The filter was immersed into SSPE solution containing 0.1% SDS, shaken at 55° C. and washed twice, further immersed into 10-fold dilution of SSPE solution containing 0.1% SDS and washed four times at 55° C. An autoradiography of the washed filter was performed using intensified screen. Clones of strongly exposed part were collected and the plaques obtained were again spread and screened by the same method hereinbefore to separate complete single clones.

The thus isolated phage clones were seven clones. Phage of all of these clones was prepared to about $1\times10^9$ pfu, purified the phage DNA using Withered Lambda Rep (Promega Corp., U.S.A.), digested by restriction enzyme EcoRI and inserted into pBluescript KS (Stratagene Inc., U.S.A.), which was digested by EcoRI in the same way. DNA sequences of the both ends of these clones were analyzed by DNA sequencer. Three clones of D5, D6 and D7 were the clone containing DNA sequence from No. 1 to 2244 in the sequence listing, SEQ ID NO: 8. A clone D4 was a clone containing DNA sequence from No. 999 to 2663 in the sequence listing, SEQ ID NO: 8. The clones D5 and D4 prepared the deletion mutant by using kilosequence deletion kit (Takara Shuzo Co., Japan) according to a description of the attached paper. Full-length cDNA base sequence of the present invention was determined using the DNA sequencer from both direction of 5'-direction and 3'-direction.

By applying with XhoI site at No. 1214 in DNA sequence in the sequence listing, SEQ ID NO: 8, D4 and D5 were digested by restriction enzyme XhoI to prepare plasmid pBSDel-1 containing full length of DNA sequence in the sequence listing, SEQ ID NO: 8.

EXAMPLE 1

Cloning of cDNA of the Novel Human Delta-2

Gene cloning of new human Delta homologue was performed using probe of the human Delta-1 gene in the sequence listing, SEQ ID NO: 8.

Probe was prepared by PCR using a template of the human Delta-1 full length gene pBSDel-1 in the sequence listing, SEQ ID NO: 8 obtained in the referential example 2, or vector pUCDL-1F, which was deposited in the above described institution. A sense primer in the sequence listing, SEQ ID NO: 9 (DNA sequence corresponding to a sequence from No. 636 to 655 in the sequence listing, SEQ ID NO: 8) and antisense primer in the sequence listing, SEQ ID NO: 10 (a complementary chain of DNA sequence corresponding to a sequence from No. 1332 to 1351 in the sequence listing, SEQ ID NO: 8) were used as primers.

A composition of solution for amplification by PCR was a composition of solution as described in the referential example 1, except for the primer and the template. PCR was conducted by the following conditions: a cycle consisting of a cycling at 95° C. for 45 seconds, at 55° C. for 45 seconds and at 72° C. for 2 minutes, a cycle of which was performed for 30 cycles, and finally the mixture was allow to stand at 72° C. for 7 minutes. A part of the PCR product was subjected to 1% agarose gel electrophoresis, stained with ethidium bromide (Nippon Gene Corp., Japan) and observed by UV light to confirm amplification of about 700 bp cDNA.

The PCR product was cut out from the agarose gel, and the DNA probe was purified according to a description of the attached sheet in Geneclean II kit (Bio101 Corp., U.S.A.) and diluted with distilled water to 25 ng/µl to prepare DNA probe having sequence shown in the sequence listing, SEQ ID NO: 11.

A human fetal lung cDNA library prepared by λgt10 (Clontech Corp., U.S.A.) was screened using the above probe according to a method described in the referential example 2. In the screening, a hybridization was conducted at 55° C. for 16 hours, with washing condition for immersing into SSC solution containing 1% SDS, shaking at room temperature and washing six times. Further, a condition immersing into SSC solution, which was diluted 3-fold containing 0.1%SDS, and washing at 55° C. was performed.

About 120 million plaques were screened in the first screening under the above condition, and as a result, about 120 plaques determined as positive, were subjected to the second screening by the similar method to separate each phage.

The isolated phage DNA was purified according to a method in the referential example 2, digested by restriction enzyme EcoRI, ligated to pBluescript KS and analyzed DNA sequence by DNA sequencer by the same method as described in the referential examaple 1.

About over half number of clones was human Delta-1 having gene sequence in the sequence listing, SEQ ID NO: 8. Among these, five clones, which were similar to but have different gene sequence of the human Delta-1, containing new sequences, which were not found in Genbank Release 98 by computer software Genetyx CD Ver 36 (Software Development Corp.) were found. Deletion mutant of DNA sequence of these clones was prepared using kilosequence deletion kit (Takara Shuzo Co., Japan) according to the attached instruction manual. Base sequence of full length cDNA of the present invention was determined from both direction of 5'-direction and 3'-direction by combining with primer walking method using the said DNA sequencer.

As a result, clone 4A encodes gene sequence from No. 526 to 3339 of DNA sequence in the sequence listing, SEQ ID NO: 4 (proviso that sequence from No. 1296 to 1515 was deleted); clone 22 encodes gene sequence from No. 1029 to 3213 of DNA sequence in the sequence listing, SEQ ID NO: 4; clone 65 encodes gene sequence from No. 754 to 3228 of DNA sequence in the sequence listing, SEQ ID NO: 4; clone 90 encodes gene sequence from No. 552 to 2618 of DNA sequence in the sequence listing, SEQ ID NO: 4; and clone 105 encodes gene sequence from No. 669 to 3339 of DNA sequence in the sequence listing, SEQ ID NO: 4 (proviso that in the clone 105, since many insertions of unknown sequences, which were not found in the other clones, were observed in many regions, it might be originated from prior splicing immature mRNA). In addition, in the clone 65, cytosine of DNA sequence No. 2294 in the sequence listing, SEQ ID NO: 4 was replaced by thymine. Therefore, serine of DNA sequence No. 647 in the sequence listing was replaced by threonine.

These clones did not, however. contain gene sequence coding full length amino acid sequence, further new probe was prepared and screening was repeated.

New probe was prepared by PCR using template of clone 4A which was isolated in the above process. A probe was prepared by using sense primer of the sequence listing, SEQ ID NO: 12 (which corresponds to a sequence from No. 526 to 545 of DNA sequence in the sequence listing, SEQ ID NO: 4) and antisense primer of the sequence listing, SEQ ID NO: 13 (which corresponds to a sequence from No. 918 to 937 of DNA sequence in the sequence listing, SEQ ID NO: 4), and by the same way as described previously. DNA sequence of this probe is shown in the sequence listing, SEQ ID NO: 14.

The screening of the cDNA library using the probe was conducted as same in the first screening procedure. Proviso that the hyphridization was performed at 65° C. for 16 hours; washing was performed by immersing into SSC solution containing 0.1% SDS with shaking at room temperature, further immersing into 10-fold diluted SSC solution containing 0.1% SDS with washing twice at 65° C.

New clones were identified by the screening. As a result of gene sequence determination, the clone P having identical sequence with DNA in the sequence listing, SEQ ID NO: 4, and the clone RA having DNA sequence from No. 263 to 2768 in the sequence listing, SEQ ID NO: 4 were determined. These two clones were isolated and identified as clones coding full length novel human Delta-2 protein. A vector containing clone P, which is ligatedin EcoRI site of pBluescript KS, is designated as pBSDL-2.

EXAMPLE 2

Organs Which Express Novel Human Delta-2

In order to search expression of the new human Delta-2 mRNA, using filters of Human Multiple Tissue Northern Blot, Human Multiple Tissue Northern Blot II, Human Multiple Tissue Northern Blot III and Human Fetal Multiple TissueNorthern Blot II (Clontech Corp., U.S.A.), for which mRNA was previously transcribed, and using DNA having sequence of the sequence listing, SEQ ID NO: 14 described in the example 1 as a probe, $^{32}P$ labeling was performed by the above mentioned procedure using the previously mentioned DNA labeling kit (Megaprime DNA labeling system: Amersham Corp., U.S.A.), hybridization was conducted according to the instruction manual attached to the above filters to detect the expression. Result is shown in FIG. 1.

As a result, two types of the expressed mRNA having length about 3.8 kb and 5 kb were found. The most strong expression in human adult tissues as expression site was the heart. Relatively strong expressions were observed in the placenta, ovary, small intestine, thyroid gland and spinal cord. Obvious expressions were observed in the skeletal muscle, lung, liver, pancreas, thymus, prostate, lymph node, trachea, adrenal gland and bone marrow. Extremely weak expressions were observed in the stomach, spleen and colon. Further no expressions were observed in the brain, kidney, testis and peripheral blood lymphocyte. Highly expression was observed in the fetal lung among the human fetal tissues. Strong expression is observed in the fetal kidney and weak expressions were observed in the fetal liver and fetal brain.

These results indicate that the novel human Delta-2 of the present invention might have function relating to the heart in adult. Further, it might have function against vascular cells due to finding of expression in the fetal lung.

EXAMPLE 3

Preparation of Expression Vectors of the Novel Human Delta-2

Using the vector pBSDL-2 coding the full length novel human Delta-2 in example 1, the expression vectors of human Delta-2 proteins mentioned in the following 1)–5) were prepared. Addition of restriction enzyme sites and insertion of short gene sequence were performed using ExSite PCR-Based Site-Directed Mutagenesis Kit (Stratagene Inc., U.S.A.) according to the instruction manual.

1) Expression Vector of Secretory Novel Human Delta-2 Protein (HD2EX)

The cDNA coding polypeptide having amino acid sequence from No. 1 to 500 in the sequence listing, SEQ ID NO: 2 was ligated into the expression vector pcDNA3 containing cytomegalovirus promoter and neomycin resistance gene to prepare the expression vector.

For preparation of expression vector of the novel human Delta-2, in order to make stable expression of gene product, EcoRI site was added in the 20 bp upper stream for 5'-direction of the initiation codon (gene sequence No. 277 in the sequence listing, SEQ ID NO: 4). Using the above Mutagenesis Kit, a plasmid pBSDL-2, which contained DNA sequence in sequence listing, SEQ ID NO: 4 and full length cDNA of human Delta-2 were set as the template, and oligonucleotides having gene sequences in sequence listing, SEQ ID NO: 15 and SEQ ID NO: 16, ware set as the primers. Then DNA adding EcoRI site in the 20 bp upper stream for 5'-direction was prepared. Hereinafter this plasmid is designated as pBSEco-DL-2.

Next, in order to add the termination codon and restriction enzyme NotI site after the extracellular C-terminal position, i.e. after DNA sequence coding amino acid sequence up to No. 500 serine residue in the sequence listing, SEQ ID NO: 2, by using the Mutagenesis Kit similarly, using the pBSEco-DL-2 as template and setting oligonucleotides having gene sequences in the sequence listing, SEQ ID NO: 17 and SEQ ID NO: 18 as primers, addition of the termination codon and NotI site were performed. Then, the resulted vector was digested by EcoRI and NotI, and about 1600 bp split gene fragment was ligated in pcDNA3, which was treated by the same restriction enzymes, to construct the expression vector. This vector was designated as pHD2EX.

2) Expression Vector of FLAG Chimera Protein of Secretory Novel Human Delta-2 (HD2EXFLAG)

The cDNA coding chimera protein having amino acid sequence from No. 1 to 500 in the sequence listing, SEQ ID NO: 2 and at this C-terminal the FLAG sequence was ligated to the expression vector pcDNA3 to prepare the expression vector.

Using pBSEco-DL-2 as template, FLAG sequence was added in the extracellular C-terminal, i.e. after serine residue at No. 500 amino acid in the sequence listing, SEQ ID NO: 2. Then, in order to add the termination condon and restriction enzyme NotI site, using the Mutagenesis Kit, and setting oligonucleotides having gene sequences in the sequence listing, SEQ ID NO: 19 and SEQ ID NO: 18 as primers, a gene coding FLAG sequence, termination codon and NotI site were added in the C-terminal. This vector was digested by EcoRI and NotI, and about 1600 bp split gene fragment was ligated to pcDNA3 treated similarly by the restriction enzyme to construct the expression vector. This vector was designated as pHD2EXFLAG.

3) Expression Vector of IgG1Fc Chimera Protein of Secretory Human Delta-2 (HD2EXIg)

A gene sequence coding polypeptide having amino acid sequence in the sequence listing, SEQ ID NO: 2 and at this C-terminal an amino acid sequence of Fc region downstream from the hinge region of human IgG1, was ligated into the expression vector pcDNA3 to prepare the expression vector.

Preparation of fused protein with immunoglobulin Fc protein was performed according to the method of Zettlmeissl et al. (Zettlmeissl et al., DNA cell Biol., 9, 347–354, 1990). A gene using genome DNA with intron was applied and the said gene was prepared by using PCR.

Human genome DNA was used as a template and genomic gene sequence coding human IgG1Fc region was subjected to PCR by using primers of an oligonucleotide having the sequence in the sequence listing. SEQ ID NO: 23 with restriction enzyme BamHI site and an oligonucleotide having the sequence in the sequence listing, SEQ ID NO: 24 with restriction enzyme XbaI site. The thus obtained about 1.4 kbp band was purified and digested by restriction enzyme BamHI and XbaI (Takara Shuzo Co., Japan), and genes were ligated to pBluescript, which was similarly treated by restriction enzyme, by using T4 DNA ligase to perform subcloning.

Later, the plasmid DNA was purified and confirmed gene sequence using sequencer, then the said gene sequence was confirmed as genomic DNA in the hinge region of heavy chain of the human IgG1. (The sequence is referred to Kabat et al., Sequence of Immunological Interest, NIH Publication No.91-3242,1991). Namely, this gene has the restriction enzyme BamHI site at 5'-terminal and XbaI site at 3'-terminal, and is cloned with BamHI site and XbaI site of pBluescript KS. Hereinafter this plasmid is designated as pBShIgFc.

Using the pBSEco-DL-2 as template, and using the Mutagenesis Kit, restriction enzyme BamHI site was added in the extracellular C-terminal, i.e. after serine at No. 500 in the sequence listing, SEQ ID NO: 3. Furthermore, in order to add restriction enzyme NotI site to the downstream for ligating DNA coding the above human immunoglobulin IgG1Fc, these sites were added by using oligonucleotides having gene sequences in the sequence listing, SEQ ID NO: 20 and SEQ ID NO: 18 and the Mutagenesis Kit. During this process, in order to not to shift the frame coding amino acid as a result of addition of BamHI site. AGC in the DNA sequence coding No. 500 serine on the DNA sequence in the sequence listing, SEQ ID NO: 4, was replaced to TCG.

The thus prepared vector was digested by NotI and BamHI, and about 1200 bp gene fragment digested and splited from the above pBShIgFc by NotI and BamHI was ligated into the digested vector to prepare finally the vector containing gene fragments coding the objective secretory human Delta-2 IgG1Fc chimera protein. Finally, this vector was digested by EcoRI and NotI and about 3000 bp split gene fragment was ligated into pcDNA3 which was treated similarly with the restriction enzymes, to construct the expression vector. This vector was designated as pHD2EXIg.

4) Expression Vector of Full Length Human Delta-2 Protein (HD2F)

The cDNA coding polypeptide from No. 1 to 659 of amino acid sequence in the sequence listing, SEQ ID NO: 4, was ligated into the expression vector pcDNA3 to prepare the expression vector.

In order to add the termination codon and restriction enzyme NotI site in C-terminal of the full length sequence, i.e. after Val at No. 659 in the sequence listing, SEQ ID NO: 3 by using pBSEco-DL-2 as template, and using the Mutagenesis kit similarly oligonucleotides having gene sequences in the sequence listing, SEQ ID NO: 21 and SEQ ID NO: 18 were set as primers, and the termination codon and NotI site were added in the C-terminal. This vector was digested by EcoRI and NotI, and about 2200 bp split gene fragment was ligated into pcDNA3, which was treated similarly by restriction enzymes, to construct the expression vector. This vector was designated as pHD2F.

5) Expression Vector of FLAG Chimera Protein (HD2FLAG) of Full Length Novel Human Delta-2

The cDNA coding chimera protein, having an amino acid sequence from No. 1 to 659 in the sequence listing, SEQ ID NO: 3 and at this C-terminal the FLAG sequence, was ligated into the expression vector pcDNA3 to prepare the expression vector.

In order to add FLAG sequence, the termination codon and restriction enzyme NotI site in the C-terminal, by using pBSEco-DL-2 as template, oligonucleotides having gene sequences in the sequence listing, SEQ ID NO: 22 and SEQ ID NO: 18 were used as primers, and a gene coding FLAG sequence and termination codon as well as NotI site were added in the C-terminal.

This vector was digested by EcoRI and NotI, and about 2100 bp split gene fragments were ligated into pcDNA3, which was treated similarly by restriction enzyme to construct the expression vector. This vector was designated as pHD2FLAG.

EXAMPLE 4

Gene Transfer of Expression Vectors Into Cells and Expression

The expression vectors prepared in Example 3 were transferred into COS-7 cell (obtained from RIKEN Cell Bank, Physical and Chemical Research Institute, Japan, RCB0539).

Cell culture before gene transfer was performed by culturing in D-MEM (Dulbecco modified Eagle's medium, GIBCO-BRL Inc., U.S.A.) 10% FCS. On a day before gene transfer, medium of cells was changed to set cell counts $5 \times 10^5$ cells/ml and cultured for overnight. On the day of gene transfer, cells were sedimented by centrifugation, washed twice with PBS (−) by centrifuge and prepared to $1 \times 10^7$ cells/ml in 1 mM $MgCl_2$ and PBS (−). Gene transfer was performed by electroporation using gene transfer device Gene-pulsar (BioRad Inc., U.S.A.). The above cell suspension 500 μl was collected in a cell exclusively for electroporation (0.4 cm), added expression vector 20 μg, and allowed to stand on ice for 5 minutes. Thereafter, voltage was charged twice under the condition of 3 μF. 450 V, and between the two charges the cell mixture was allowed to stand at room temperature for 1 minute. After 5 minutes allowed to stand on ice, cells were spread in the culture medium, diameter 10 cm previously added 10 ml of medium, and cultured at 37° C. in 5% carbon dioxide incubator.

Next day, the cultured supernatant solution was removed, washed the cells adhered to the dish twice with PBS(−) 10 ml. In cases of expression vectors pHD2EX, pHD2EXFLAG and pHD2EXIg, serum-free D-MEM 10 ml was added and cultured for further 7 days. Cultured supernatant solution was recovered and was replaced the buffer to PBS (−) by Centricon 30 (Amicon Inc., U.S.A.) and simultaneously the solution was concentrated to 10-fold to obtain cell cultured supernatant solution.

In cases of pHD2F and pHD2FLAG, medium was changed by D-MEM containing 10% FCS, and cultured further 3 days to prepare cell lysate. Thus, $2 \times 10^6$ cells were suspended in the cell lysis buffer [50 mM Hepes (pH 7.5), 1% Triton X100, 10% glycerol, 4 mM EDTA, 50 μg/ml Aprotinin, 100 μM Leupeptin, 25 μM Pepstatin A and 1 mM PMSF] 200 μl, allowed to stand on ice for 20 minutes and centrifuged at 14000 rpm for 20 minutes to remove supernatant solution to obtain cell lysate.

Using the thus obtained samples, expression of proteins were detected by Western blotting.

Namely, concentrated cultured supernatants or cell lysates were subjected to SDS-PAGE using an electrophoresis tank and polyacrylamide gel for SDS-PAGE (gradient gel 5–20%) (ACI Japan Inc., Japan) according to the attached instruction manual. Samples were prepared by treatment in boiling water for 5 minutes with 2-mercaptoethanol (2-ME) for reduction, and non-reduced condition without taking the above treatment. As a markers Rainbow Marker (higher molecular weight, Amersham Inc.) was used. Sample buffer solution and electrophoresis buffer were prepared with reference to the attached leaflet. When the SDS-PAGE was finished, acrylamide gel was transcribed to PVDF membrane filter (BioRad Inc., U.S.A.) using the Mini Trans Blot Cell (BioRad Inc.).

The thus prepared filter was shaken overnight at 4° C. in the Blockace (Dainippon Pharm. Co., Japan) or TBS-T [20 mM Tris, 137 mM NaCl (pH 7.6) and 0.1% Tween 20] containing 5% bovine serum albumin (Sigma Co., U.S.A.) for blocking. Thereafter, according to the explanation of the attached leaflet of the ECL Western blotting detection system (Amersham Inc., U.S.A.); anti-human Delta-2 mouse monoclonal antibody described in Example 6 or mouse monoclonal antibody Anti-FLAG M2 (Kodak Inc. U.S.A.) for FLAG chimera (HD2EXFLAG and HD2FLAG) was used as primary antibody and peroxidase labeled anti-mouse Ig sheep antibody (Amersham Corp., U.S.A.) was reacted as secondary antibody. In case of IgG chimera, peroxidase labeled anti-human Ig sheep antibodies (Amersham Inc., U.S.A.) was reacted.

Reaction time for antibodies was 1 hour at room temperature, and at an interval of each reaction, washing was performed by shaking in TBS-T at room temperature for 10 minutes for three times. After the final washing, the filter was immersed in the reaction solution of ECL-Western blotting detection system (Amersham Inc., U.S.A.) for 5 minutes, and wrapped in polyvinylidene chloride wrapping film to expose X-ray film.

As the result, in the sample with treatment of reduction, the bands showing a protein obtained by transfer of pHD2EX and pHD2EXFLAG were detected a band of about 65 kD and a protein obtained by transfer of pHD2EXIg was detected a band of about 95 kD. In the non-reduced sample, the bands showing protein obtained by transfer of pHD2EXIg were detected slightly smeared bands at 150 kD to 200 kD, mainly about 180 kD, which showed about 2-fold of the reduction stage, consequently, dimer was formed.

In these experiments, however, although cell lysate and cultured supernatant of COS-7 cells, to which pcDNA3 vector was transferred as a control, were tested, no bands reacted against anti-human Delta-2 mouse monoclonal antibody, anti-FLAG antibody, and anti-human Ig antibody were detected.

Therefore, these five expression vectors can produce the objective polypeptides.

EXAMPLE 5

Purification of Secretory Novel Human Delta-2 Proteins of Gene Transfer Cells

Cultured supernatants of COS-7 cells containing HD2EXFLAG or HD2EXIg, both of which expression was detected by the method in example 4, were prepared in large scale, and each chimera protein was purified by affinity column.

In case of HD2EXFLAG, 2 liter of the cultured supernatant obtained by the method in the example 4 was passed through a column packed with Anti-FLAG M2 Affinity Gel (Eastman Kodak, U.S.A.) and the chimera protein was adsorbed in a column by an action of affinity between FLAG sequence of the chimera protein and Anti-FLAG antibody of the gel. Column, a disposable column (BioRad Inc., U.S.A.) with inner diameter of 10 mm, was used with packing the above gel 5 ml. A circulation system consisting of medium bottle→column→peristaltic pump→medium bottle was set up. The circulation was run by a flow 1 ml/min. for 72 hours. Thereafter the column was washed with PBS (−) 35 ml and eluted with 0.5 M Tris-glycine (pH 3.0) 50 ml. The eluate of 25 fractions, each 2 ml, was collected into the tube, and each fraction was neutralized by 200 μl of 0.5 M Tris-HCl (pH 9.5) previously added in each tube.

The eluate fraction, each 10 μl of the secretory FLAG chimera protein, which was purified by the above method, was subjected to reduction treatment described in Example 4. SDS-PAGE electrophoresis by 5–10% gradient polyacrylamide gel was performed. After finishing the electrophoresis, silver staining was conducted by using Wako silver stain kit II (Wako Pure Chemicals, Japan) according to the explanation of the attached leaflet. As a result, a band of HS2EXFLAG was detected in the eluate fractions from No. 4 to 8. Molecular weight thereof was identical with the result of Western blotting of anti-FLAG antibody obtained in the example 4. Therefore, purified HD2EXFLAG was obtained.

In the IgG1Fc chimera protein, i.e. HD2EXIg, 2 liters of the cultured supernatant was adsorbed to Protein A Sepharose column (Pharmacia Inc., Sweden) according to the same method as of FLAG chimera protein to collect the eluate fractions. Using a part of eluate as same as in FLAG chimera protein, a determination of the eluate fraction, identification of the size and detection of the purity were performed by SDS-PAGE electrophoresis and silver staining in the reduced condition. As a result, bands were detected in the eluate fraction from No. 4 to 15. The size thereof is identical with the result of Western blotting using anti-human Ig. Therefore, purified HD2EXIg was obtained.

Molecular weight of the thus purified HD2EXFLAG was further analyzed in details by SDS-PAGE. The molecular weight was confirmed as two bands, one of which was 65.8 KD and the other was 61.7 KD. These different two bands having different molecular weights were transcribed into PVDF according to the method in the example 4, and ten amino acids of N-terminal amino acid sequence were determined by amino acid sequencer (ABI Corp., U.S.A.). As a result, each amino acid sequence was identical with the amino acid sequence from No. 1 to 10 in the sequence listing, SEQ ID NO: 1. This result indicates that difference in molecular weight might be due to difference in attached sugar chain. Similarly, in the purified HD2EXIg, two bands having slightly different molecular weight were confirmed and were thought to be due to the same reason.

EXAMPLE 6

Preparation of Antibody Recognizing Novel Human Delta-2

HD2EXFLAG, purified by the method in Example 5, was used as immunogen, and rabbits were immunized. After assaying antibody titer, whole blood was collected and serum was obtained. Anti-human Delta-2 rabbit polyclonal antibody was prepared by using the Econopack serum lgG purification kit (BioRad Inc., U.S.A.) with reference to the attached instruction manual.

HD2EXFLAG purified by a method described in the example 5 was used as immunogen, and mouse monoclonal antibody was prepared according to the explanation in the textbook. The purified HD2EXFLAG was administered in Balb/c mice (Nippon SLC CO., Japan), 10 μg/mouse, immunized intracutaneously and subcutaneously. After second immunization, increased serum titer was confirmed by collecting blood ophthalmologically, the third immunization was performed. Subsequently, the spleens of mice were collected and fused with mouse myeloma cells P3X63Ag8 (ATCC TIB9) using polyethylene glycol. Hybridoma was selected by HAT medium (Immunological and Biological Research Institute, Japan), and the hybridoma strains, which produced antibody specifically recognizing extracellular region of novel human Delta-2 in the medium, were isolated by enzyme immunoassay. The hybridoma strains producing mouse monoclonal antibody, which specifically recognized novel human Delta-2, were established.

The novel human anti-human Delta-2 monoclonal was purified and prepared by using Mab Trap GII (Pharmacia Inc., Sweden) according to the explanation of the attached instruction manual from the supernatant of the thus established hybridoma.

Using the monoclonal antibodies, affinity column was prepared. Preparation of the affinity column was performed according to the instruction manual attached to the CNBr activated Sephadex 4B (Pharmacia Inc., Sweden). A column, 2 cm$^2$×1 cm, containing gel 2 ml, was prepared. A concentrated solution of the supernatant of the cultured COS-7 cells, to which pHD2EX was gene transferred, was passed through the column, for which anti-human Delta-2 monoclonal antibody was bound, at 20 ml/hr, subsequently PBS (−) 15 ml was passed at the same flow rate and washed the column. Finally, the product was eluted by a mixture of 0.1 M sodium acetate and 0.5 M NaCl (pH 4.0). The eluate, each 1 ml fraction, was collected, and was neutralized by adding 1M Tris-HCl (pH 9.1) 200 μl for each fraction.

SDS-PAGE of each purified protein was conducted under reduced condition according to the method described in the example 4, followed by silver staining and Western blotting to estimate molecular weight. As a result, HD2EX of about 65 kD was purified from concentrated supernatant of the cultured COS-7 cells, to which pHD2EX was gene transferred. Consequently, the novel human Delta-2 protein can be purified by the affinity column.

EXAMPLE 7

Effects of HD2EXIg to Colony Formation of Blood Undifferentiated Cells

In order to observe physiological action of HD2EXIg on blood undifferentiated cells, CD34 positive cells were cultured in the serum-free semi solid medium in the presence of HD2EXIg and known cytokines, and number of colony forming cells were observed.

Human umbilical cord blood or adult human normal bone marrow blood was treated by the silica solution (Immunological and Biological Research Institute, Japan) according to the attached instruction manual, then the low density cellular fraction (<1.077 g/ml) was fractionated by densitometric centrifugation of Ficoll pack (Pharmacia Inc., Sweden) to prepare mononuclear cells, and CD34 positive cells of human umbilical cord blood or human normal bone marrow blood was isolated from the mononuclear cells.

Separation of CD34 positive cells was performed by using Dynabeads M-450 CD34 and DETACHaBEADS CD34 (Dynal Inc., Norway) according to attached instruction manual. After separation, the purity was measured as follows. Cells were stained by FITC labeled CD34 antibody HPCA2 (Beckton-Deckinson Inc., U.S.A.) and examined by flow-cytometer (FACSCalibur, Beckton-Deckinson, U.S.A.). Purity above 85% was confirmed for use.

The thus isolated CD34 positive cells were suspended homogeneously to form 400 cells/ml of the medium hereinbelow, and spread in the 35 mm dish (Falcon Inc., U.S.A.), then cultured for 2 weeks in carbon dioxide incubator at 37° C. under 5% carbon dioxide, 5% oxygen, 90% nitrogen and 100% humidity. The thus formed blood colonies were counted under the invert microscope.

A medium used is α-medium (GIBCO-BRL, U.S.A.), containing 2% deionized bovine serum albumin (BSA, Sigma, U.S.A.), 10 μg/ml human insulin (Sigma, U.S.A.), 200 μg/ml transferrin (Sigma, U.S.A.), $10^{-5}$ M 2-mercaptoethanol (Nakarai Tesk Co., Japan), 160 μg/ml soybean lecithin (Sigma, U.S.A.), 96 μg/ml cholesterol (Sigma, U.S.A.) and 0.9% methylcellulose (Wako Pure Chemicals, Japan).

To the above medium, the novel human Delta-2 extracellular Ig chimera protein (HD2EXIg) was added to the final concentration of 1 μg/ml. For control, human IgG1 (Athens Research and Technology Inc., U.S.A.) was added with the same concentration in order to observe effect of IgGFc region.

Conditions of simultaneously added cytokines were as follows: 100 ng/ml human SCF (Intergen Inc., U.S.A.), 10 ng/ml human IL-3 (Intergen Inc., U.S.A.), and 100 ng/ml human IL-6 (Intergen Inc., U.S.A.).

As a result, in the control group, number of colony formation was 42±5 per 400 cells, and in HD2EXIg added group, number of colony formation was 21±3, which showed significant suppression of colony formation. Result indicates that the novel human Delta-2 of the present invention has an action on the blood undifferentiated cells.

EXAMPLE 8

Action of HD2EXIg on LTC-IC of Blood Undifferentiated Cells in Serum Free Liquid Culture For confirmation of physiological action of HD2EXIg on the undifferentiated blood cells in the liquid culture, umbilical cord blood mononuclear CD34 positive cells were cultured in serum-free medium in the presence of HD2EXIg and known cytokines. Culture has continued for 2 weeks, and at the present day on 2 weeks culture, changes of LTC-IC, which was thought to be most undifferentiated blood cells, were confirmed.

For comparative studies, a control experiment without adding HD2EXIg and an experiment with addition of HD1EXIg, which was IgG chimera protein (HD1EXIg) and was found to have LTC-IC activity in the similar experiment disclosed in WO 97/19172 in the name of present inventors, were conducted. Preparation of HD1EXIg was performed according to the description of WO 97/19172.

Sixteen thousands and two hundreds CD34 positive cells of umbilical cord blood mononuclear cells isolated by a method described in the example 7 were cultured in the following medium. Numbers of LTC-IC were counted in the four experimental groups of the pre-culture group, HD2EXIg added group, HD1EXIg added group and control group. Number of cells and number of colony forming cells were also counted.

Culture was performed in the basal medium of α-medium, to which 2% BSA, 10 μg/ml human insulin, 200 μg/ml transferrin, 40 μg/ml low density lipoprotein, $10^{-5}$ M 2-mercaptoethanol, 100 ng/ml human SCF, 10 ng/ml human IL-3 and 100 ng/ml human IL-6 were added. To the HD2EXIg added group, purified HD2EXIg 1 μg/ml was added; to the HD1EXIg added group, purified HD1EXIg 1 μg/ml was added; and to the control group, the above human IgG1 was added. Exchange of medium was conducted twice a week with changing half volume.

LTC-IC was measured according to a method of Sutherland et al. (Blood, 74, 1563-, 1989; Proc. Natl. Acad. Sci., U.S.A., 87, 3584-, 1990). In details, refer to WO 97/18172 in the name of the present inventors.

Total cell counts were measured by counting numbers of living cells microscopically using trypan blue (Gibco BRL, U.S.A.). Numbers of colony forming cells were performed according to a method in the example 7 using the following medium. The medium is α-medium, to which 30% fetal calf serum (FCS, ICN Biomedical Japan, Japan), 1% BSA, $10^{-5}$ M 2-mercaptoethanol, 0.9% methylcellulose (Wako Pure Chemicals, Japan), 100 ng/ml human SCF, 10 ng/ml human IL-3, 100 ng/ml human IL-6, 2U/ml human EPO (Chugai Seiyaku Co., Japan) and 10 ng/ml human G-CSF (IntergenInc., U.S.A.).

Result is shown in Table 1.

Table 1 Effect of the human Delta-2 of the present invention on liquid culture

TABLE 1

| Effect of the human Delta-2 of the present invention on liqid culture | | | |
|---|---|---|---|
| | Total cell counts | Colony forming cells | LTC-IC |
| Pre-culture group | 16200 | 2500 | 150 |
| Post-culture group | | | |
| Control | 445000 | 23000 | 3.3 |
| HD1EXIg | 395000 | 16700 | 9.3 |
| HD2EXIg | 418000 | 16000 | 16.2 |

Result indicates that HD2EXIg has maintenance activity for numbers of LTC-IC as compared with the control group. Further, the activity is stronger than HD1EXg.

EXAMPLE 9

Binding and Separation of HD2EXIg for Blood Undifferentiated Cells

Binding of purified HD2EXIg with human T cell type blood cell strain Jurkat and human umbilical cord blood mononuclear CD34 positive cells was studied. In the binding experiment, human Delta-1 chimera protein (HD1EXIg), which was found to have the similar activity by the present inventors, was used as comparative experiment as like in the example 8.

Jurkat cells, $1 \times 10^6$ cells, were suspended in Hank's balanced salt solution (Gibco BRL, U.S.A.) containing 2% FCS and 10 mM Hepes. HD2EXIg, HD1EXIg or human IgG1, each 1 μg/ml, were added therein and allowed to stand at 4° C. for 3 hours. Cells were washed with the Hank's solution by centrifugation, and PE (phycoerythrin) labeled sheep anti-human IgG monoclonal antibody 1 μg/ml was added, then the mixture was allowed to stand in ice-cooling for 30 minutes. Thereafter, the mixture was washed twice with the Hank's solution. Analysis was performed using the flow cytometer FACScalibur (Beckton and Dekinson, U.S.A.).

Figure 2:
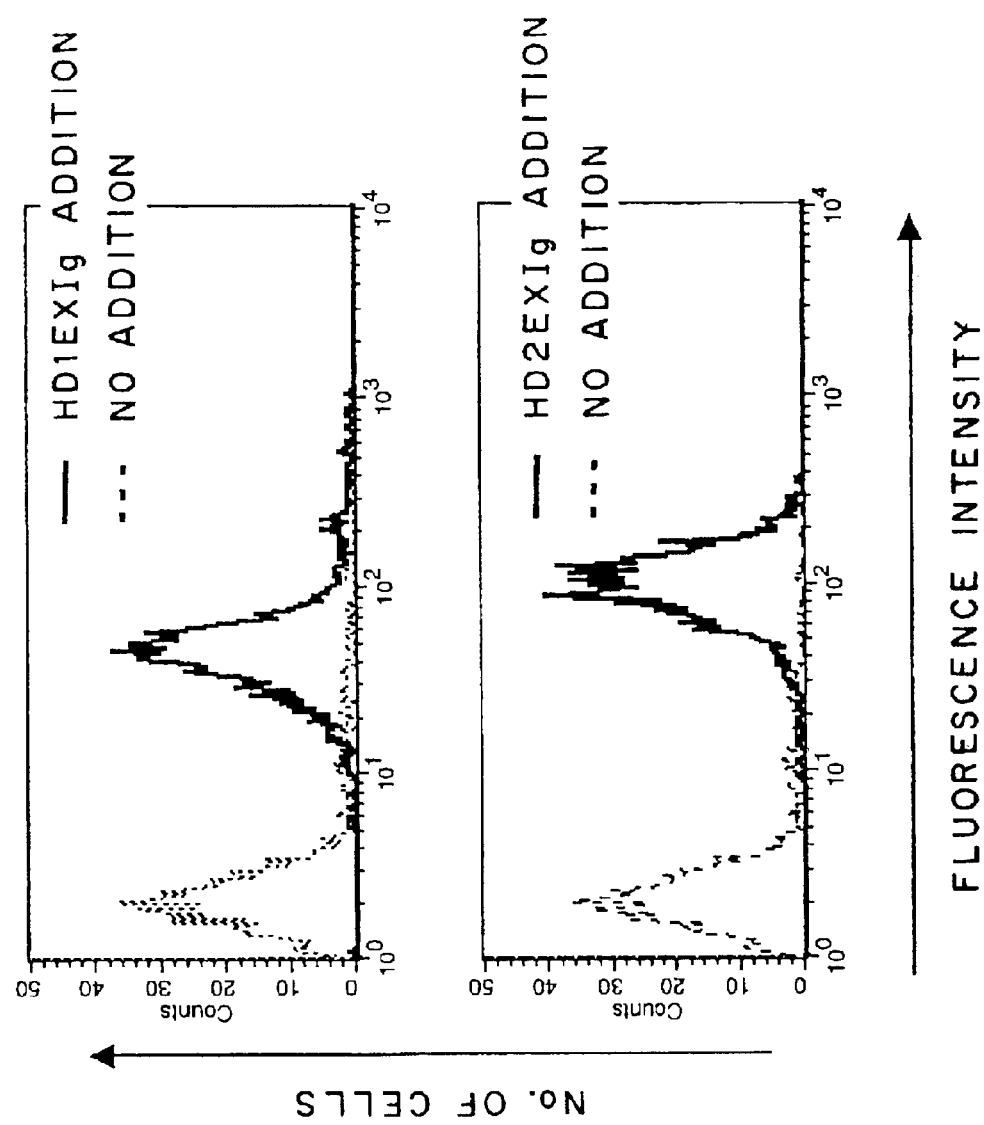
FIG. 2: Binding of HD2EXIG of the present invention and of HD1EXIG as a control to the human origin T cell type cell line Jurkat.

Results are shown in FIG. 2. A vertical axis indicates cell counts and a horizontal axis indicates fluorescence intensity. The upper indicates result of the control HD1EXIg and the lower indicates result of HD2EXIg of the present invention. Staining with HD1EXIg or HD2EXIg is shown by solid line and staining with human IgG1, a control group, is shown by a broken line. In all cases, binding with Jurkat cells was observed. Observing the binding activities, fluorescence intensity of HD2EXIg of the present invention was stronger than that of HD1EXIg of the upper. Lean fluorescence intensity of HD2EXIg was about twice-fold stronger than that of HD1EXIg. As a result, HD2EXIg is bound with Jurkat cells stronger than HD1EXIg.

Binding activity to the human umbilical cord blood mononuclear CD34 positive cells isolated by the method described in the example 7 was determined by the same staining method. In this case, staining with FITC labeled anti-human CD34 antibody HPCA-2 (Beckton and Dekinson Corp., U.S.A.) was performed simultaneously in the second antibody labeling. Data is shown only CD34 positive, i.e. FITC positive fraction.

Figure 3:
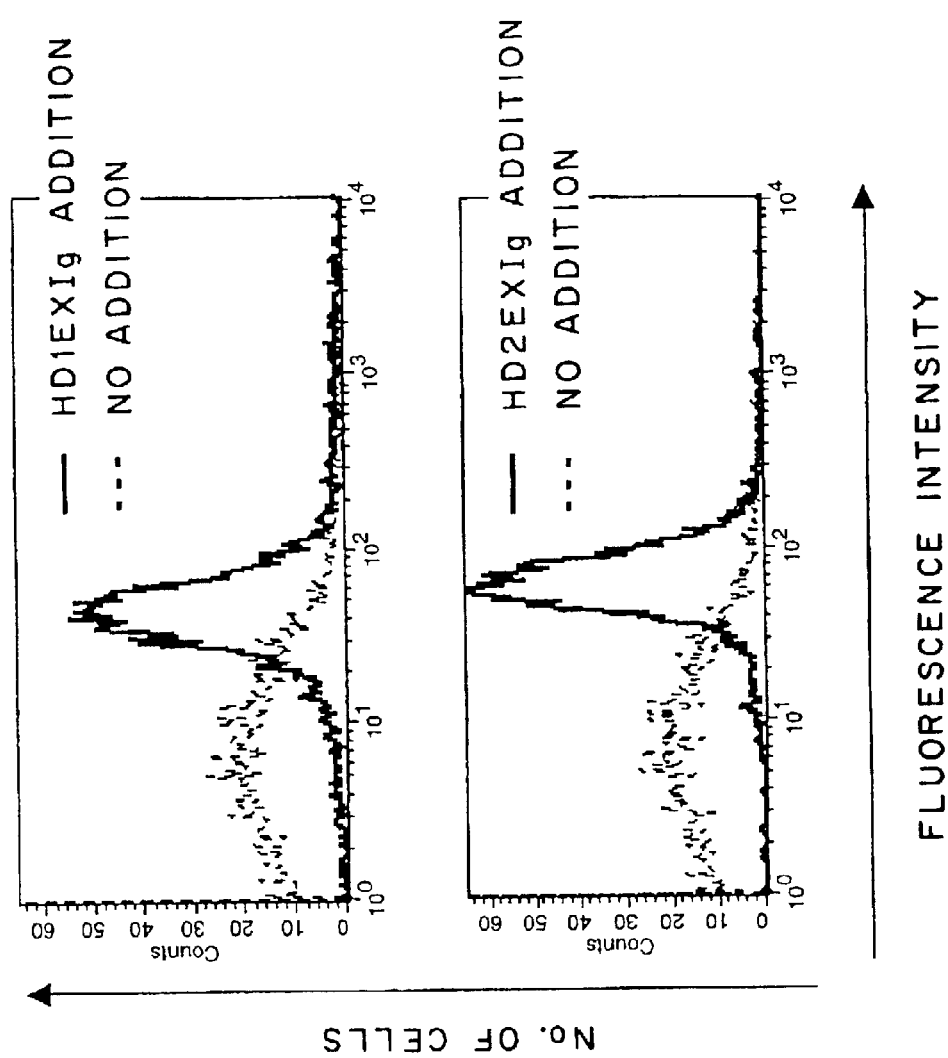
FIG. 3: Binding of HD2EXIG of the present invention and of HD1EXIG as a control to CD34 positive cells from human umbilical cord blood mononuclear cells.

Result is shown in FIG. 3. Result indicates that HD2EXIg and HD1EXIg similarly bind with CD34 positive cells, and binding activity of HD2EXIg is two-fold stronger than that of HD1EXIg.

HD2EXIg stained cells were treated by cell sorter FACS-vantage (Beckton and Dekinson Corp., U.S.A.) according to the attached instruction manual to separate cells of HD2EXIg positive fraction.

EXAMPLE 10

Effect of Cocultivation with the Novel Human Delta-2 Expression Cells on Blood Undifferentiated Cells FLAG chimera protein expression vector pHD2FLAG of the full length novel human Delta-2 prepared in the example 3 was gene transferred into mouse cell strain Balb3T3 (Physical and Chemical Institute, Cell Development Bank RCB0005) according to a method described in the example 4 and selection was conducted by G418 (Gibco BRL Inc., U.S.A.) according to the known method to obtain clones. The thus obtained clones were confirmed their expression of FLAG chimera protein of the full length human Delta-2 according to the method described in the example 4 and clones, for which expression was confirmed, were used in the following experiments. The clone is designated as Balb/HD2FLAG.

The umbilical cord blood mononuclear CD34 positive cells obtained by the method in the example 7 and Balb/HD2FLAG were cocultured. Cocultivation with Balb3T3, for which no gene transfer was made, was conducted as a control.

Culture conditions are:
1) Balb3T3 without gene transfer and no hematopoietic factor,
2) Balb/HD2FLAG and no hematopoietic factor,
3) Balb3T3 without gene transfer and hematopoietic factor, and
4) Balb/HD2FLAG and hematopoietic factor.

Medium used is α-medium added with 10% FCS and $10^{-5}$ M 2-mercaptoethanol. In the hematopoietic factor added group, 100 ng/ml human SCF, 10 ng/ml human IL-3 and 100 ng/ml human IL-6 were added. Cultivation is continued for 2 weeks and medium exchange was performed three times a week for half volume. Prior to cocultivation with human blood cells, previously cultured Balb3T3 cells were irradiated with 250 KV Peak X-ray to suppress cell growth.

Numbers of colony forming cells and LTC-IC were measured in the pre-cultivation and the experimental groups 1) to 4).

Results were as follows.

In the pre-cultivation, total cell counts were 20000 cells. Among those, colony forming cells were 3200 cells and LTC-IC was 220 cells.

In 1), colony forming cells and LTC-IC counts were very few for impossible to measure.

In 2), numbers of colony forming cells were very few for impossible to measure. LTC-IC counts were 105 cells.

In 3), numbers of colony forming cells were 26500 and LTC-IC counts were 90.

In 4), numbers of colony forming cells were 38000 and LTC-IC counts were 120.

Analysis of breakdown of colony forming cells in 3) and 4) indicated that in 3), only granulocyte colony was observed, however in 4) erythroblast was also observed. Consequently, difference in number of colony forming cells were due to difference in number of erythroblast colony.

As a result, Balb/HD2FLAG cell has colony forming action, especially erythroblast colnoy grwoth action as well as LTC-IC maintenance action. Result indicates that using the human Delta-2 expression vector of the present invention, cells having hematopoietic cell maintaining activity can be produced.

EXAMPLE 11

Preparation of Material Immobilized with the Novel Human Delta-2 and Its Effect

Sepharose gel immobilized with HD2EXIg prepared in the example 5 was prepared. Sepharose gel used was CNBr activated Sepharose gel (Pharmacia Inc., Sweden). HD2EXIg was immobilized according to the attached instruction manual.

The thus prepared gel and the umbilical cord blood mononuclear CD34 positive cells isolated by the method in the example 7 were cultured for twenty-four hours. Cultivation was conducted in the same medium as in the example 10. In the control group, Sepharose gel immobilized with BSA was prepared. After cultivation, numbers of colony forming cells were measured according to the method in the example 8. As a result, in the gel immobilized with HD2EXIg, numbers of colony forming cells were decreased about 40%.

Consequently, the material, to which human Delta-2 of the present invention was immobilized, has an action against hematopoietic cells.

EXAMPLE 12

Effect of the Novel Human Delta-2 on Vascular Endothelial Cells

Fourth subculture of vascular endothelial cells, i.e. normal human aortic endothelial cells and normal human lung artery endothelial cells (Kurabo Co., Japan), were used. Cells were spread 5000 cells/well in 96 well-plate for cell culture (Falcon Inc., U.S.A.) at the culture of third subculture and were cultured in the low serum medium for endothelial cell growth (HuMedia-EG2, Kurabo Co., Japan) containing human recombinant EGF (Kurabo Co., Japan) 10 ng/ml and human recombinant FGF-B 5 ng/ml. At the same time, the novel human Delta-2 extracellular chimera protein (HD2EXIg) was added for final concentration of 1 μg/ml. In the comparative experiment group, same concentration of human IgG1 (Athens Research and Technology Corp., U.S.A.) was added in order to observe effect of IgGFc region. In the control group, cultivation was conducted without adding protein except for HuMedia-EG2. Cultivation was conducted at 37° C., under 5% carbon dioxide gas and 100% humidity for 3 days, and numbers of cells were counted.

Counting for numbers of vascular endothelial cells was performed by using NR reagent set (Kurabo Co., Japan), the principle of which was developed by Borenfreund and Purerner (Journal of Tissue Culture Methods 9 (1), 7–9, 1984), i.e. neutral red method, which was applied the phenomenon that vital staining pigment neutral red (3-amino-7-dimethylamino-2-methylphenazine) can only permeate through cell membrane of living cells to accumulate in the lysosome. Absorption at 540 nm was measured by Immunoreader (NJ-2000, Nippon Intermed Co., Japan). As a result, in case of aortic endothelial cells, optical density (OD) in the control group was 0.18±0.02, and OD in the human IgG1 added group was almost same grade, 0.17±0.02, however OD in the HD2EXIg added group was significantly low grade, 0.11±0.01. In case of pulmonary artery endothelial cells, optical density (OD) in the control group was 0.16±0.02, and OD in the human IgG1 added group was almost same grade, 0.16±0.02, however OD in the HD2EXIg added group was significantly low grade, 0.08±0.01. These results indicate that HD2EXIg suppresses growth of vascular endothelial cells.

EXAMPLE 13

Preparation of Drug Formulation

Each polypeptide shown in the example 5, 1 mg and human serum albumin (Midori Juji Co.) 5 mg were dissolved in distilled water 1 ml. The solution was aseptically passed through 0.22 μm filter for sterilization, dispensed into a vial and lyophilized to prepare drug formulation.

Effect of the Invention

The novel human Delta-2 molecule of the present invention can be used for effective chemicals for suppression of growth and differentiation of undifferentiated cells such as undifferentiated blood cells, and can be used as pharmaceuticals and medical care materials.

---

What is claimed is:

1. An isolated DNA encoding an amino acid sequence comprising the sequence of SEQ ID NO: 1.

2. The isolated DNA according to claim 1 encoding an amino acid sequence comprising the sequence of SEQ ID NO: 2.

3. The isolated DNA according to claim 2 comprising the nucleotide sequence of nucleotides 335–1854 of SEQ ID NO: 4.

4. The isolated DNA according to claim 1 encoding an amino acid sequence comprising the sequence of SEQ ID NO: 3.

5. The isolated DNA according to claim 4 comprising the nucleotide sequence of nucleotides 355–2331 of SEQ ID NO: 4.

6. The isolated DNA according to claim 1 comprising the nucleotide sequence of nucleotides 355–927 of SEQ ID NO: 4.

7. A recombinant DNA comprising the DNA of claim 1, ligated to a vector which can express DNA in a host cell.

8. An isolated cell transformed by the recombinant DNA of claim 7.

9. A method comprising transforming human cells with a recombinant DNA encoding an amino acid sequence comprising the sequence of SEQ ID NO: 1 to obtain the transformed cells of claim 8.

10. A process for the production of a polypeptide comprising an amino acid sequence of SEQ ID NO: 1, said method comprising culturing the cells of claim 8 under conditions in which said polypeptide is expressed, and isolating said polypeptide.

* * * * *